(12) United States Patent
Abdou

(10) Patent No.: US 8,568,453 B2
(45) Date of Patent: Oct. 29, 2013

(54) SPINAL STABILIZATION SYSTEMS AND METHODS OF USE

(76) Inventor: Samy Abdou, San Diego, CA (US)

(*) Notice: Subject to any disclaimer, the term of this patent is extended or adjusted under 35 U.S.C. 154(b) by 1392 days.

(21) Appl. No.: 12/011,772

(22) Filed: Jan. 29, 2008

(65) Prior Publication Data
US 2008/0281359 A1 Nov. 13, 2008

Related U.S. Application Data

(60) Provisional application No. 60/898,010, filed on Jan. 29, 2007, provisional application No. 60/921,570, filed on Apr. 3, 2007.

(51) Int. Cl.
*A61B 17/70* (2006.01)

(52) U.S. Cl.
USPC .......... 606/248; 606/279; 606/277; 606/71

(58) Field of Classification Search
USPC .......... 606/60, 246–269, 272, 273, 278, 279, 606/70, 71, 282, 286–291, 293, 297
See application file for complete search history.

(56) References Cited

U.S. PATENT DOCUMENTS

| | | | |
|---|---|---|---|
| 3,648,691 A | 3/1972 | Lumb et al. | |
| 4,448,191 A | 5/1984 | Rodayansky et al. | |
| 4,554,914 A | 11/1985 | Kapp et al. | |
| 4,611,582 A | 9/1986 | Duff | |
| 5,011,484 A | 4/1991 | Breard | |
| 5,234,432 A | 8/1993 | Brown | |
| 5,250,055 A | 10/1993 | Moore et al. | |
| 5,261,910 A | 11/1993 | Warden et al. | |
| 5,304,178 A | 4/1994 | Stahurski | |
| 5,312,405 A * | 5/1994 | Korotko et al. | 606/278 |
| 5,437,669 A * | 8/1995 | Yuan et al. | 606/278 |
| 5,496,318 A | 3/1996 | Howland et al. | |
| 5,609,634 A | 3/1997 | Voydeville | |
| 5,645,599 A | 7/1997 | Samani | |
| 5,683,392 A * | 11/1997 | Richelsoph et al. | 606/272 |
| 5,722,976 A | 3/1998 | Brown | |
| 5,725,582 A | 3/1998 | Bevan et al. | |
| 5,836,948 A | 11/1998 | Zucherman et al. | |
| 5,860,977 A | 1/1999 | Zucherman et al. | |
| 6,238,396 B1 * | 5/2001 | Lombardo | 606/86 A |
| 6,312,431 B1 | 11/2001 | Asfora | |
| 6,355,038 B1 | 3/2002 | Pisharodi | |
| 6,364,883 B1 | 4/2002 | Santilli | |

(Continued)

FOREIGN PATENT DOCUMENTS

WO    WO 2008/106140    9/2008

OTHER PUBLICATIONS

Anderson T. et al., "Pain 5 years after instrumented and non-instrumented posterolateral lumbar spinal fusion" Eur Spine J Aug. 2003;12(4):393-9. Epub May 20, 2003.

(Continued)

*Primary Examiner* — Pedro Philogene
*Assistant Examiner* — Lynnsy Schneider
(74) *Attorney, Agent, or Firm* — Gazdzinski & Associates, PC

(57) ABSTRACT

An orthopedic device is adapted to fixate the spinous processes of vertebral bones. The device includes at least one bone engagement member. When implanted, a bone engagement member is located on each side of a spinous process and adapted to forcibly abut the side of each spinous process.

59 Claims, 24 Drawing Sheets

(56) References Cited

U.S. PATENT DOCUMENTS

| | | | |
|---|---|---|---|
| 6,554,831 B1* | 4/2003 | Rivard et al. | 606/253 |
| 6,582,433 B2 | 6/2003 | Yun | |
| 6,589,243 B1* | 7/2003 | Viart et al. | 606/250 |
| 6,613,050 B1* | 9/2003 | Wagner et al. | 606/250 |
| 6,802,844 B2* | 10/2004 | Ferree | 606/258 |
| 7,048,736 B2 | 5/2006 | Robinson et al. | |
| 7,090,674 B2 | 8/2006 | Doubler et al. | |
| 7,361,179 B2 | 4/2008 | Rousseau et al. | |
| 7,628,799 B2* | 12/2009 | Richelsoph et al. | 606/250 |
| 7,806,911 B2 | 10/2010 | Peckham | |
| 7,842,074 B2 | 11/2010 | Abdou | |
| 7,854,752 B2* | 12/2010 | Colleran et al. | 606/279 |
| 8,241,330 B2* | 8/2012 | Lamborne et al. | 606/248 |
| 2003/0040746 A1 | 2/2003 | Mitchell et al. | |
| 2003/0167058 A1* | 9/2003 | Shluzas | 606/61 |
| 2003/0216736 A1* | 11/2003 | Robinson et al. | 606/61 |
| 2004/0162558 A1* | 8/2004 | Hegde et al. | 606/61 |
| 2004/0260291 A1 | 12/2004 | Jensen | |
| 2005/0277924 A1* | 12/2005 | Roychowdhury | 606/61 |
| 2006/0015181 A1 | 1/2006 | Elberg | |
| 2006/0036246 A1 | 2/2006 | Carl et al. | |
| 2006/0064095 A1 | 3/2006 | Senn | |
| 2006/0085069 A1 | 4/2006 | Kim | |
| 2006/0089646 A1 | 4/2006 | Bonutti | |
| 2006/0149278 A1 | 7/2006 | Abdou | |
| 2006/0161152 A1 | 7/2006 | Ensign et al. | |
| 2006/0217712 A1* | 9/2006 | Mueller et al. | 606/61 |
| 2006/0235387 A1 | 10/2006 | Peterman | |
| 2006/0241601 A1* | 10/2006 | Trautwein et al. | 606/61 |
| 2006/0241614 A1 | 10/2006 | Bruneau et al. | |
| 2006/0247640 A1 | 11/2006 | Blackwell et al. | |
| 2006/0276792 A1* | 12/2006 | Ensign et al. | 606/61 |
| 2006/0293662 A1 | 12/2006 | Boyer, II et al. | |
| 2007/0093823 A1 | 4/2007 | Booth et al. | |
| 2007/0118132 A1* | 5/2007 | Culbert et al. | 606/72 |
| 2007/0162001 A1 | 7/2007 | Chin et al. | |
| 2007/0179500 A1 | 8/2007 | Chin et al. | |
| 2007/0233082 A1 | 10/2007 | Chin et al. | |
| 2007/0270840 A1 | 11/2007 | Chin et al. | |
| 2008/0039837 A1 | 2/2008 | Gambale | |
| 2008/0125813 A1* | 5/2008 | Erickson et al. | 606/246 |
| 2008/0147190 A1 | 6/2008 | Dewey et al. | |
| 2008/0177326 A1* | 7/2008 | Thompson | 606/277 |
| 2008/0183211 A1 | 7/2008 | Lamborne et al. | |
| 2008/0183218 A1 | 7/2008 | Mueller et al. | |
| 2008/0243186 A1 | 10/2008 | Abdou | |
| 2008/0243189 A1* | 10/2008 | Purcell et al. | 606/264 |
| 2008/0269904 A1* | 10/2008 | Voorhies | 623/17.16 |

OTHER PUBLICATIONS

Asazuma T. et al., "Intersegmental spinal flexibility with lumbosacral instrumentation. An in vitro biomechanical investigation" Spine (Phila PA 1976) Nov. 1990; 15(11):1153-8.

Bendo J.A. et al., "Instrumented posterior arthrodesis of the lumbar spine in patients with diabetes mellitus" Am J Orthop (Belle Mead NJ) Aug. 2000;29(8):617-20.

Benz R.J. et al., "Current techniques of decompression of the lumbar spine" Clin Orthop Relat Res Mar. 2001;(384):75-81.

Branch C.L., "Posterior lumbar interbody fusion with the keystone graft: technique and results" Surg Neurol May 1987;27(5):449-54.

Chen W. et al., "Surgical treatment of adjacent instability after lumbar spine fusion" Spine (Phila Pa 1976) Nov. 15, 2001;26(22):E519-24.

Chiba M. et al., "Short-segment pedicle instrumentation. Biomechanical analysis of supplemental hook fixation" Spine (Phila Pa 1976) Feb. 1, 1996;21(3):288-94.

Cobo Soriano J. et al., "Predictors of outcome after decompressive lumbar surgery and instrumented posterolateral fusion" Eur Spine J Feb. 5, 2010; [Epub ahead of print].

Dawson E.G. et al., "Intertransverse process lumbar arthodesis with autogenous bone graft" Clin Orthop Relat Res Jan.-Feb. 1981;(154):90-6.

Deguchi M. et al., "Biomechanical comparison of spondylolysis fixation techniques" Spine (Phila Pa 1976) Feb. 15, 1996; 24(4):328-33.

Dove J., "Internal fixation of the lumbar spine. The Hartshill rectangle" Clin Orthrop Relat Res Feb. 1986;(203):135-40.

Fischgrund J.S. et al., "1997 Volvo Award winner in clinical studies. Degenerative lumbar spondylolisthesis with spinal stenosis: a prospective, randomized study comparing decompressive laminectomy and arthrodesis with and without spinal instrumentation" Spine (Phila Pa 1976) Dec. 15, 1997;22(24):2807-12.

Freeman B.J., et al., "Posterior lumbar interbody fusion combined with instrumented postero-lateral fusion: 5-year results in 60 patients" Eur Spine J Feb. 2000;9(1):42-6.

Gibson J., "Surgery for degenerative lumbar spondylosis" Cochrane Database Syst Rev 2005;(4):CD001352. Epub Oct. 19, 2005.

Gill G.G., "Long-term follow-up evaluation of a few patients with spondylolisthesis treated by excision of the loose lamina with decompression of the nerve roots without spinal fusion" Clin Orthop Relat Res Jan.-Feb. 1984;(182):215-9.

Greenough C.G. et al., "Instrumented posterolateral lumbar fusion. Results and comparison with anterior interbody fusion" Spine (Phila Pa 1976) Feb. 15, 1993;23(4):479-86.

Gunzburg R. et al., "The conservative surgical treatment of lumbar spinal stenosis in the elderly" Eur Spine J Oct. 2003;12 Suppl 20:S176-80. Epub Sep. 5, 2003.

Hajek P.D. et al., "Biomechanical study of C1-C2 posterior arthrodesis techniques" Spine (Phila Pa 1976) Feb. 2003;18(2):173-7.

Katz J.N. et al., "Lumbar laminectomy alone or with instrumented or noninstrumented arthrodesis in degenerative lumbar spinal stenosis. Patient selection, costs, and surgical outcomes" Spine (Phila Pa 1976) May 15, 1997;22(10):1123-31.

Krag M.H. et al., "An internal fixator for posterior application to short segments of the thoracic, lumbar, or lumbosacral spine. Design and testing." Clin Orthop Relat Res Feb. 1986; (203):75-98.

Lin P.M., "Internal decompression for multiple levels of lumbar spinal stenosis: a technical note" Neurosurgery Oct. 1982; 11(4):546-9.

Lorenz M. et al., "A comparison of single-level fusions with and without hardware" Spine (Phila Pa 1976) Aug. 1991; 16 (8 Suppl): S445-8.

Luque E.R., "Segmental spinal instrumentation of the lumbar spine" Clin Orthop Relat Res Feb. 1986;(203):126-34.

Madan S. et al., "Circumferential and posterolateral fusion for lumbar disc disease" Clin Orthop Relat Res Apr. 2003;(409):114-23.

Madan S. et al., "Outcome of posterior lumbar interbody fusion versus posterolateral fusion for spondylolytic spondylolisthesis" Spine (Phila Pa 1976) Jul. 15, 2002;27(14):1536-42.

O'Leary P.F. et al., "Distraction laminoplasty for decompression of lumbar spinal stenosis"Clin Orthop Relat Res Mar. 2001;(384):26-34.

Polly D. et al., "Surgical treatment for the painful motion segment: matching technology with the indications: posterior lumbar fusion" Spine (Phila Pa 1976) Aug. 15, 2005;30(16 Suppl):S44-51.

Rompe J.D. et al., "Degenerative lumbar spinal stenosis. Long-term results after undercutting decompression compared with decompressive laminectomy alone or with instrumented fusion" Neurosurg Rev Oct. 1999;22(2-3):102-6.

Rousseau M. et al., "Predictors of outcomes after posterior decompression and fusion in degenerative spondylolisthesis" Eur Spine J Feb. 2005;14(1):55-60. Epub Jun. 10, 2004.

Sidhu K.S. et al., "Spinal instrumentation in the management of degenerative disorders of the lumbar spine" Clin Orthop Relat Res Feb. 1997;(335):39-53.

Smith M.D. et al., "A biomechanical analysis of atlantoaxial stabilization methods using a bovine model. C1/C2 fixation analysis" Clin Orthop Relat Res May 1993;(290):285-95.

(56) References Cited

OTHER PUBLICATIONS

Stambough J. et al., "Instrumented one and two level posterolateral fusions with recombinant human bone morphogenetic protein-2 and allograft: a computed tomography study" Spine (Phila Pa 1976) Jan. 1, 2010; 35(1):124-9.

Stambough J.L., "Lumbosacral instrumented fusion: analysis of 124 consecutive cases" J Spinal Disord Feb. 1999;12(1):1-9.

Swanson K. et al., "The effects of an interspinous implant on intervertebral disc pressures" Spine (Phila Pa 1976) Jan. 1, 2003;28(1):26-32.

Vamvanij V. et al., "Surgical treatment of internal disc disruption: an outcome study of four fusion techniques" J Spinal Disord Oct. 1998;11(5):375-82.

Voor M.J. et al., "Biomechanical evaluation of posterior and anterior lumbar interbody fusion techniques" J Spinal Disord Aug. 1998;11(4):328-34.

Wang J. et al., "Comparison of CD Horizon Spire spinous process plate stabilization and pedicle screw fixation after anterior lumbar interbody fusion. Invited submission from the Joint Section Meeting on Disorders of the Spine and Peripheral Nerves, Mar. 2005" J Neurosurg Spine 2006, Feb.; 4(2):132-6.

Wang J. et al., "SPIRE spinous process stabilization plate: biomechanical evaluation of a novel technology. Invited submission from the Joint Section Meeting on Disorders of the Spine and Peripheral Nerves, Mar. 2005" J Neurosurg Spine Feb. 2006;4(2):160-4.

\* cited by examiner

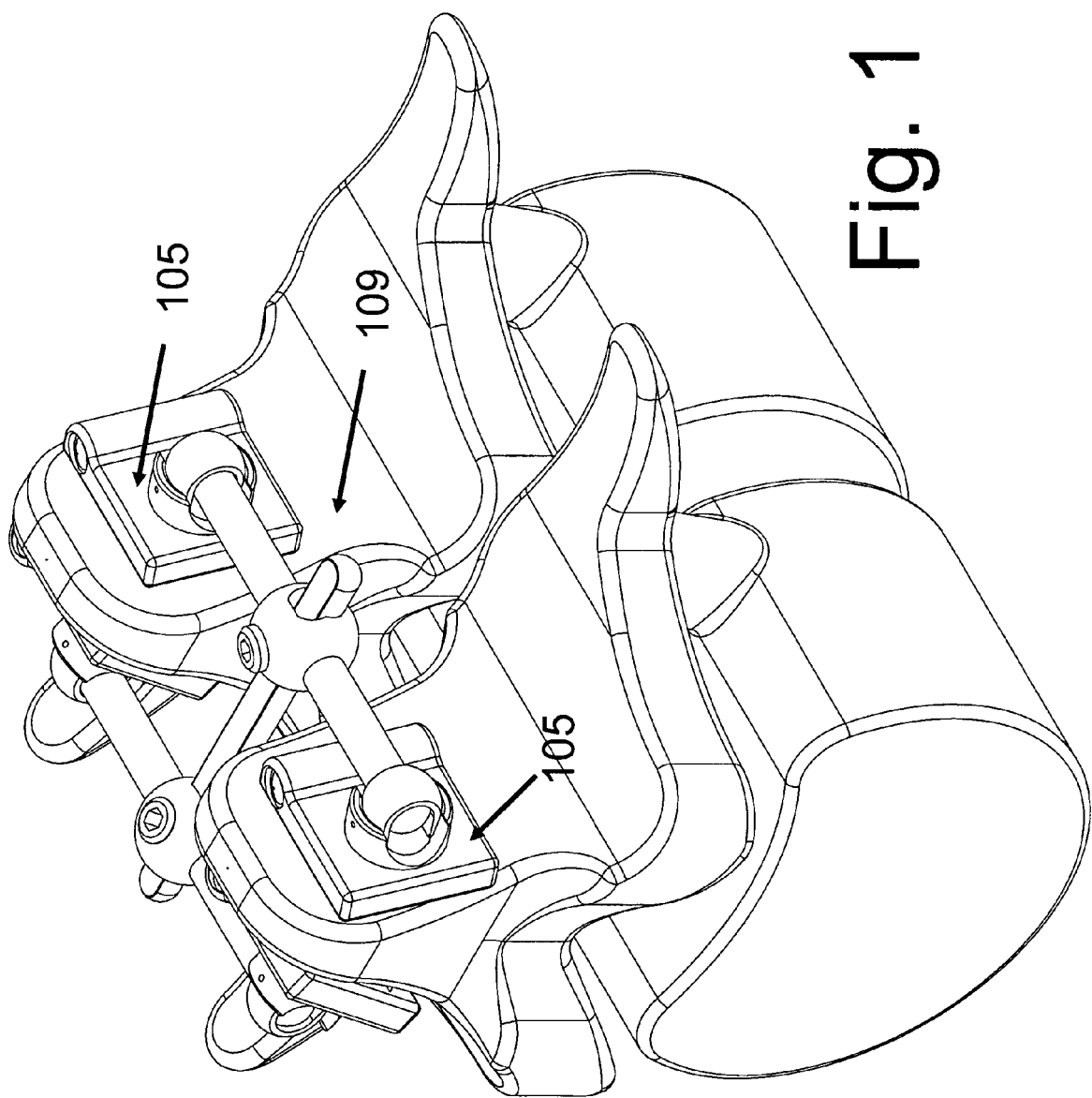

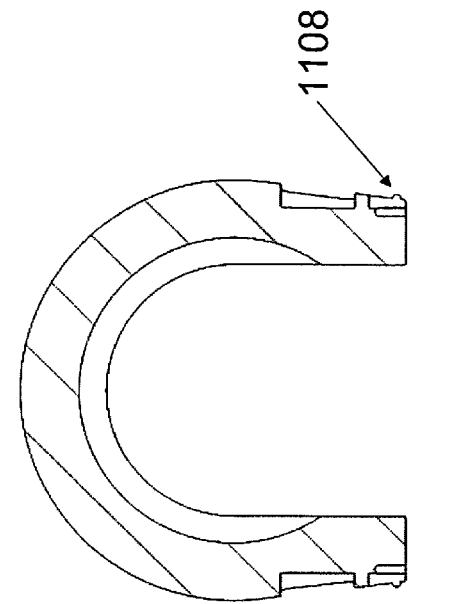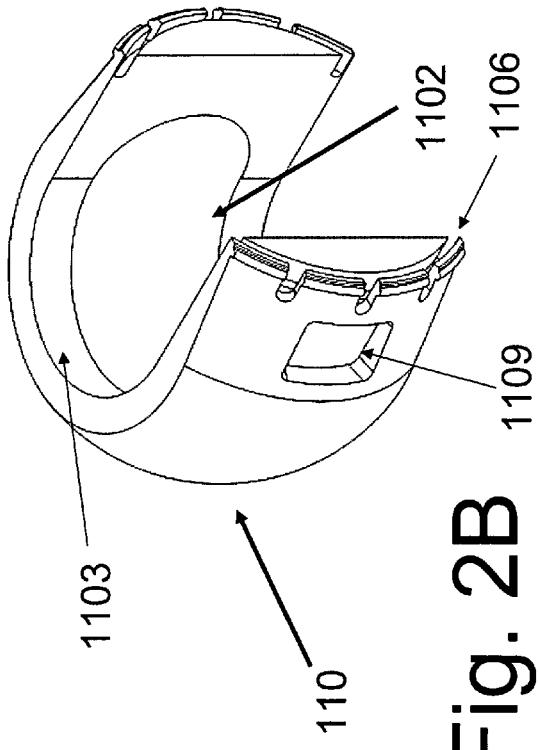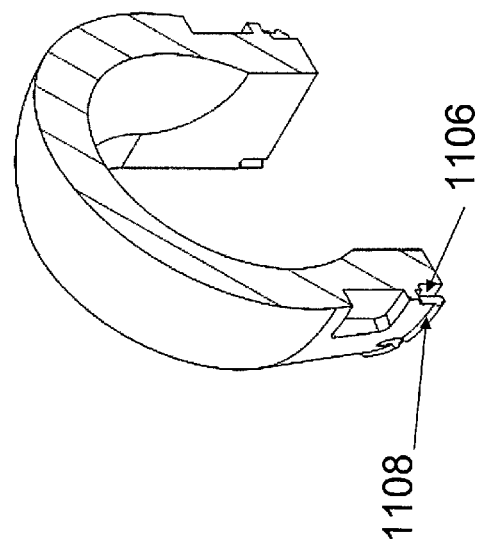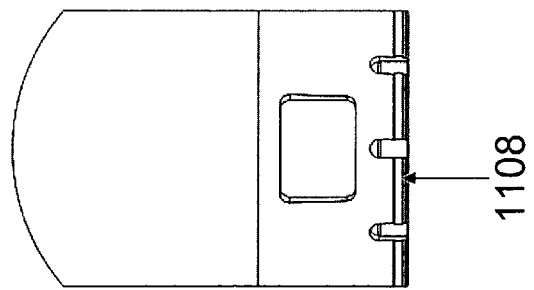
Fig. 2B

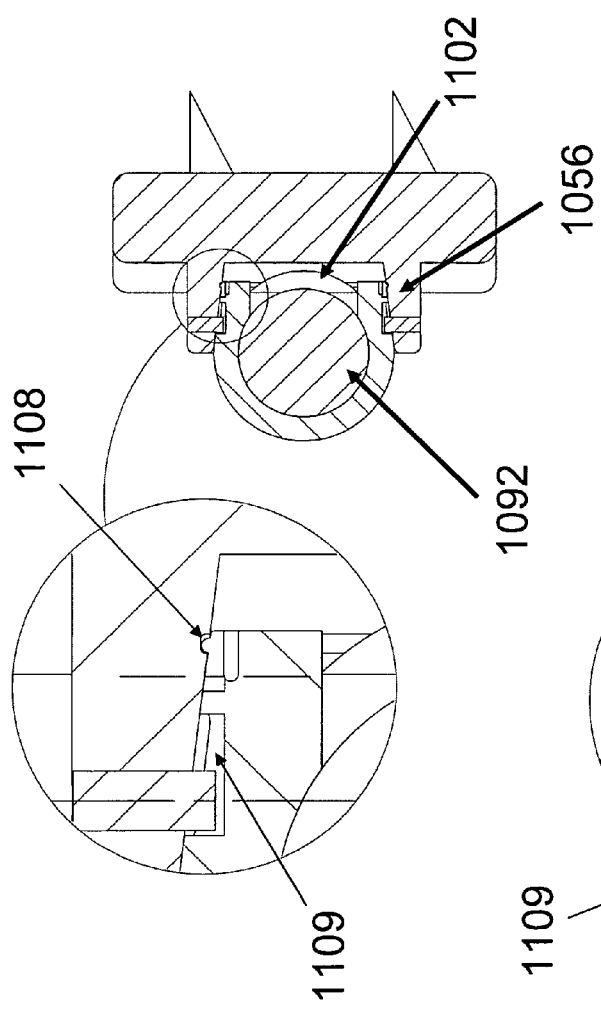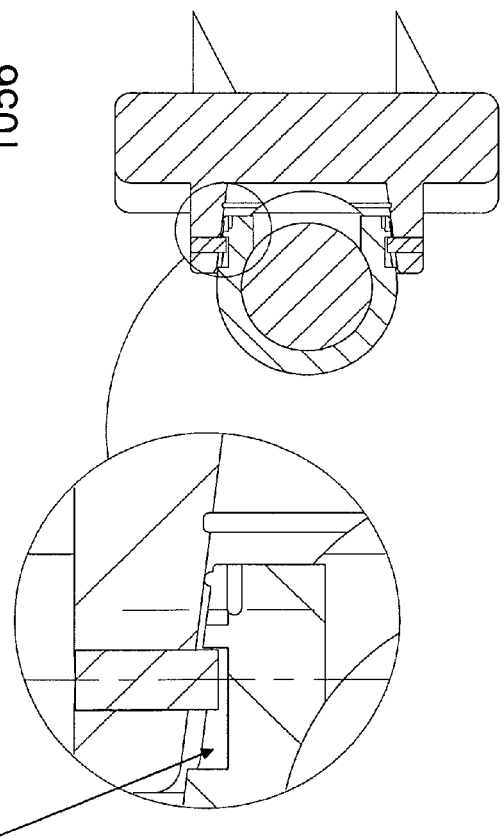

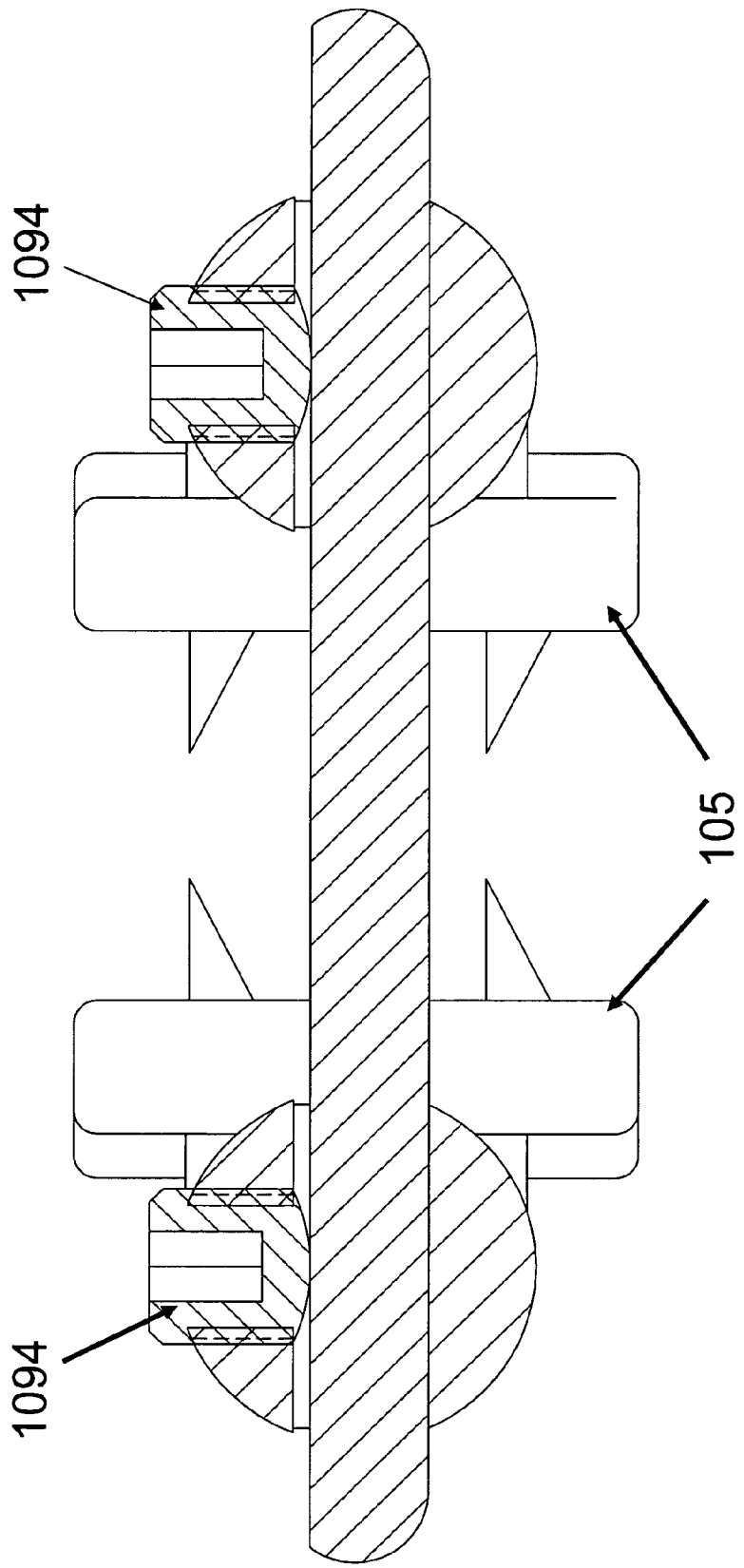

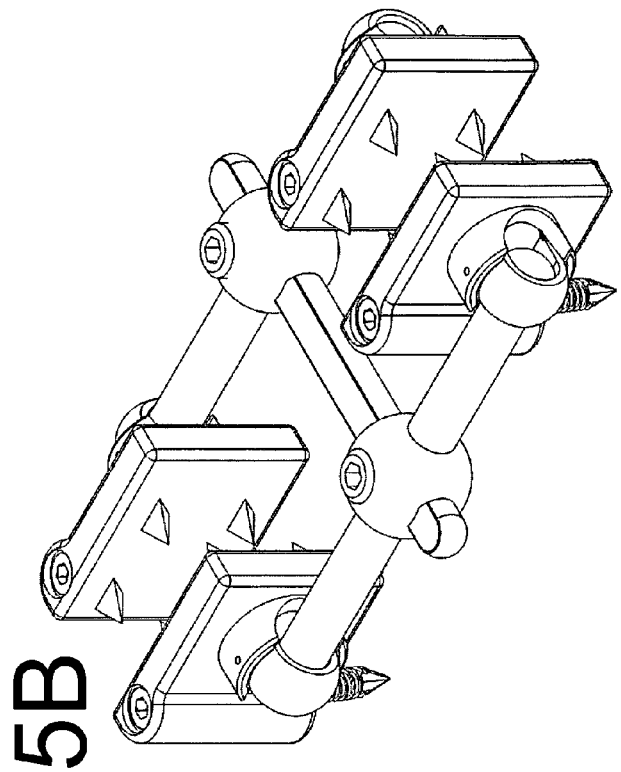
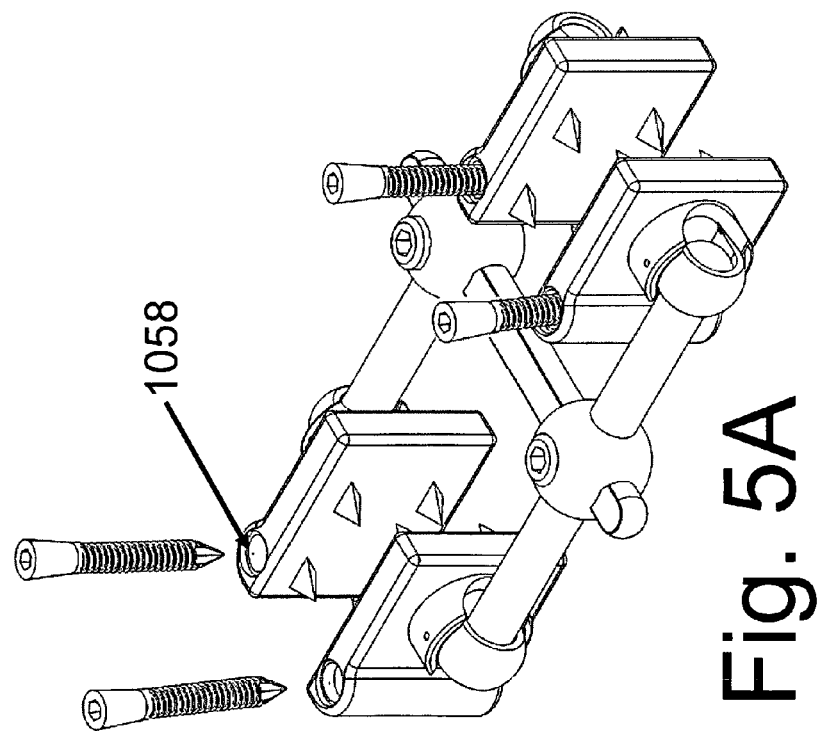

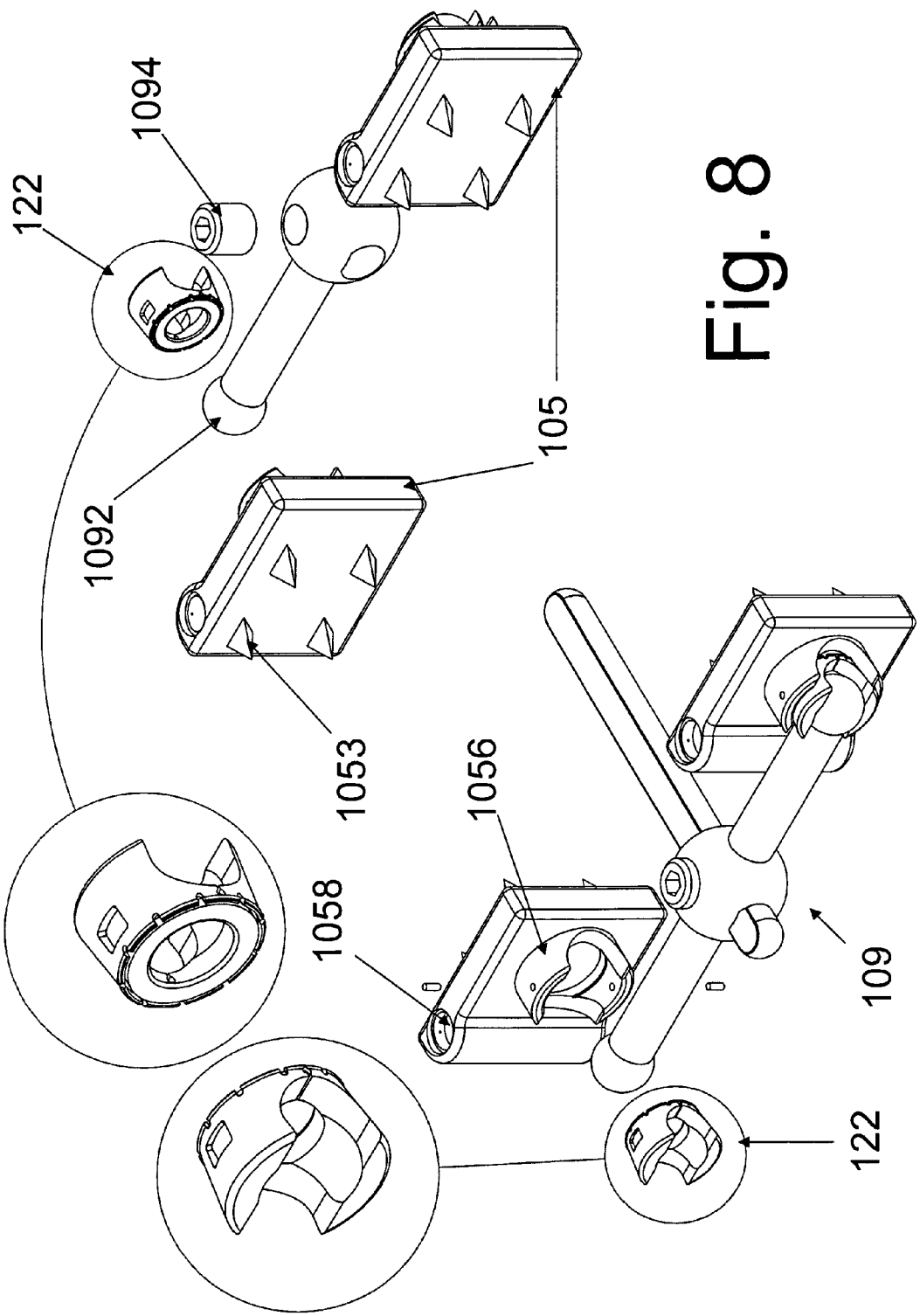

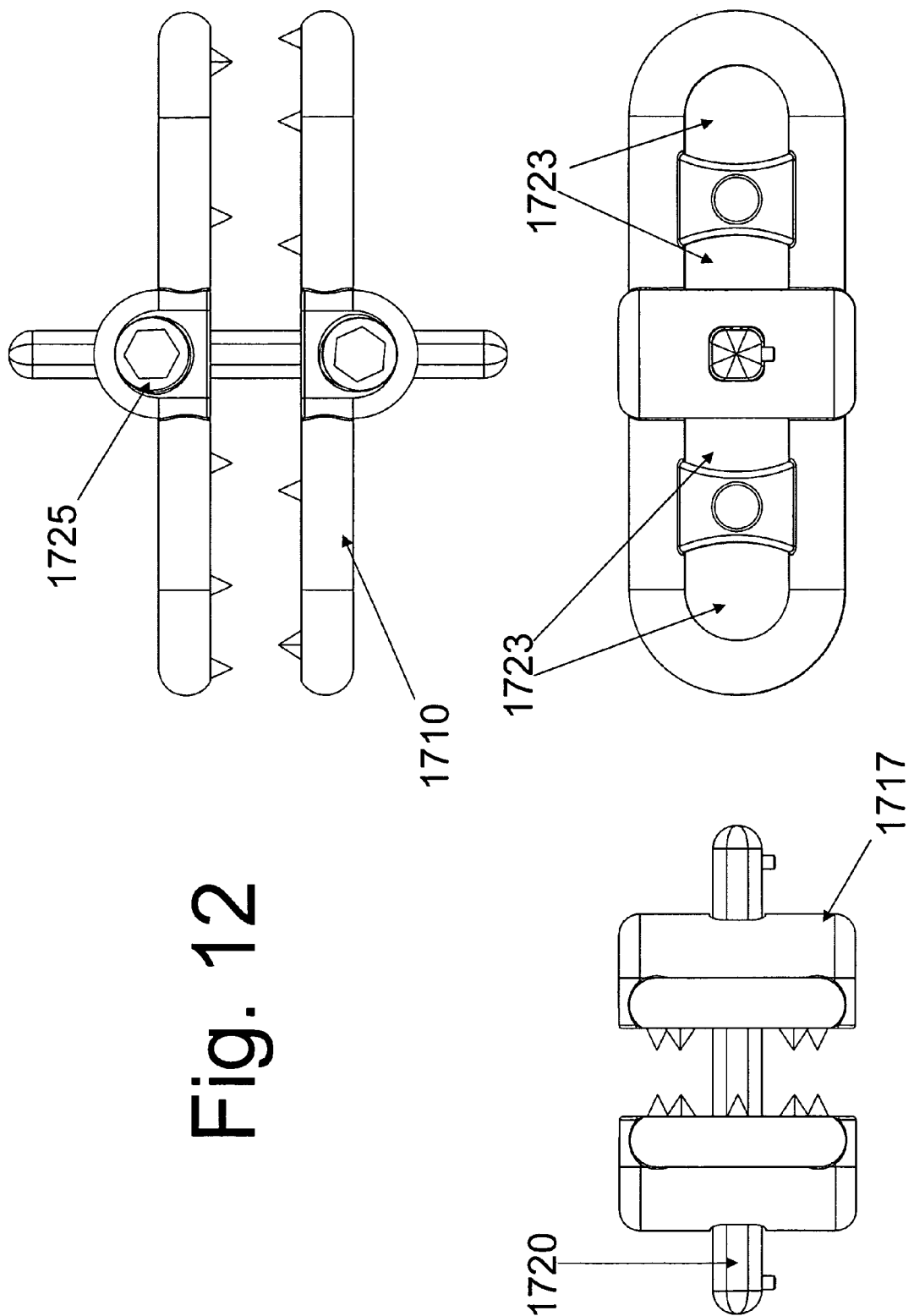

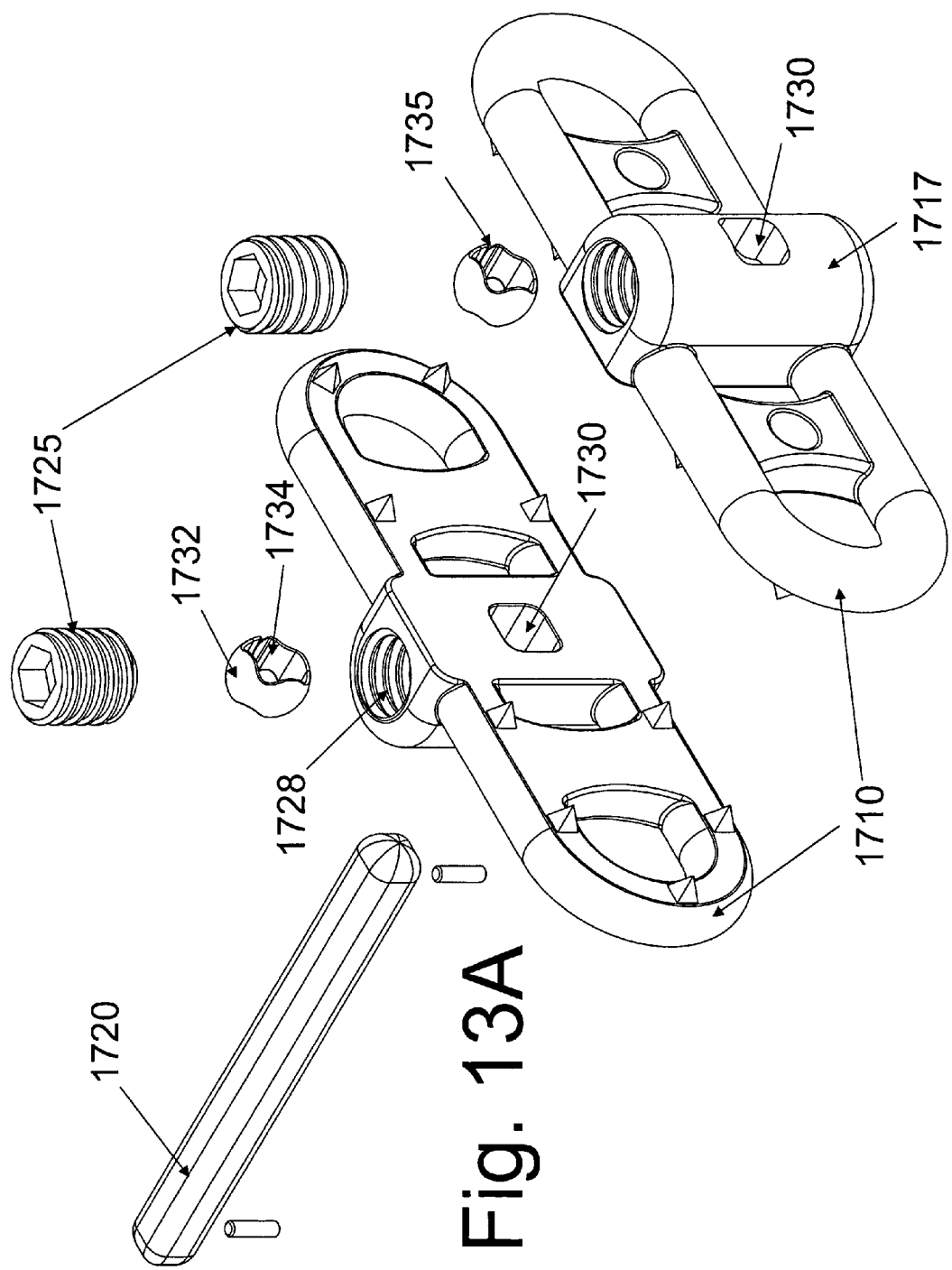

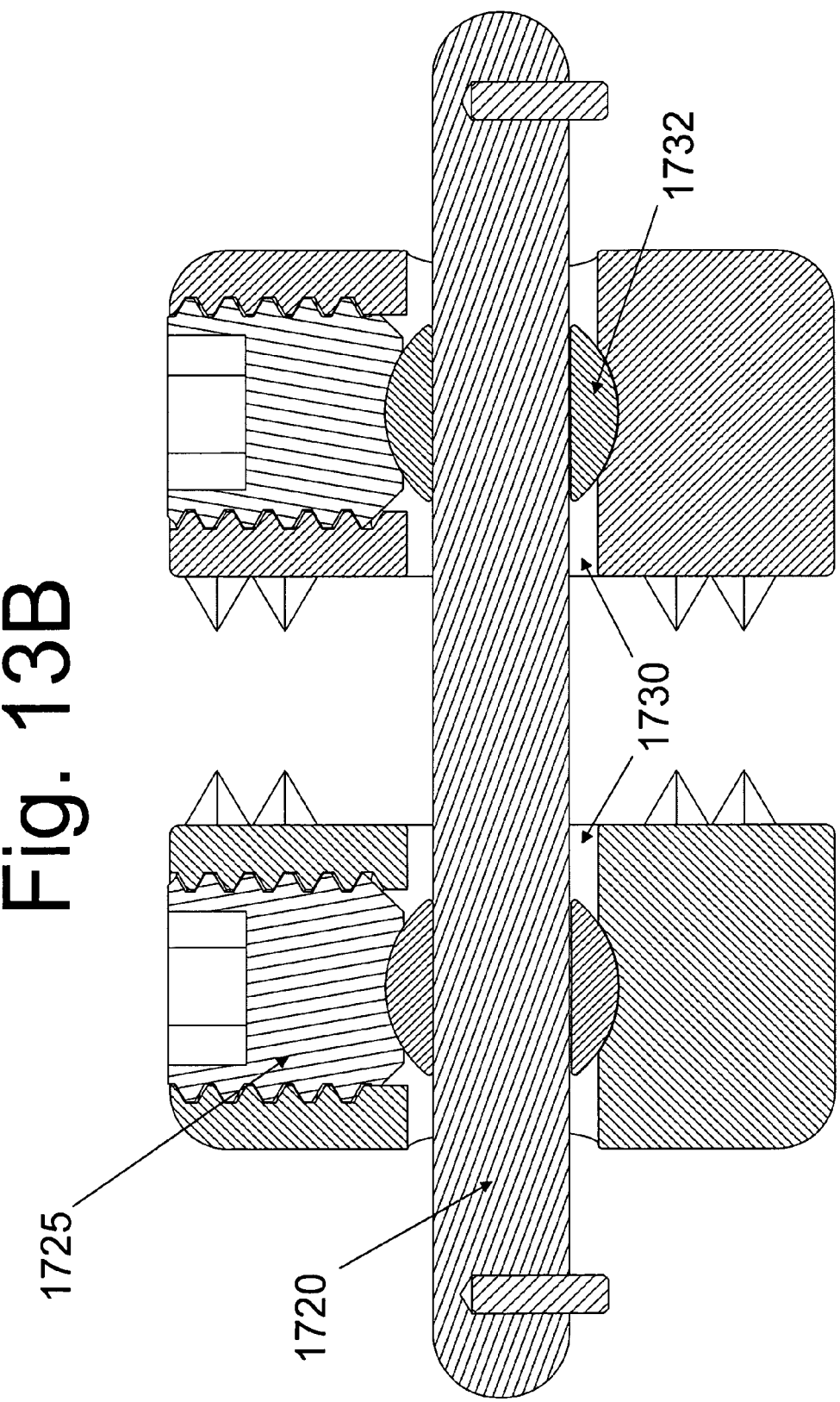

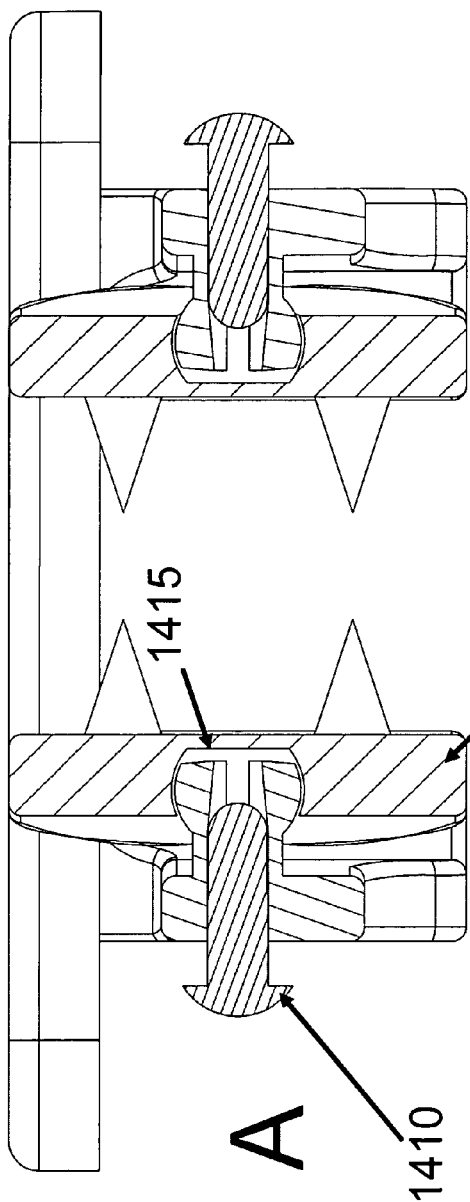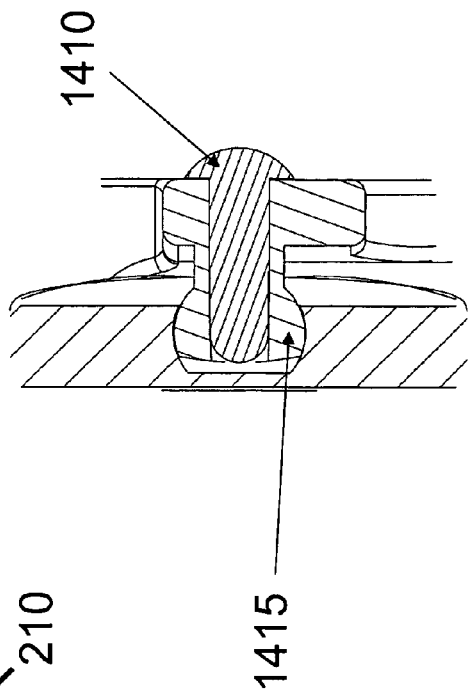
Fig. 19 A
Fig. 19 B

SPINAL STABILIZATION SYSTEMS AND METHODS OF USE

REFERENCE TO PRIORITY DOCUMENTS

This application claims priority of co-pending U.S. Provisional Patent Application Ser. No. 60/898,010 filed Jan. 29, 2007, and U.S. Provisional Patent Application Ser. No. 60/921,570 filed Apr. 3, 2007. Priority of the aforementioned filing dates is hereby claimed and the disclosures of the Provisional Patent Applications are hereby incorporated by reference in their entirety.

BACKGROUND

The present disclosure relates to devices and methods that permit fixation and stabilization of the bony elements of the skeleton. The devices permit adjustment and maintenance of the spatial relationship(s) between neighboring bones. Depending on the specifics of the embodiment design, the motion between adjacent skeletal segments may be limited or completely eliminated.

Spinal degeneration is an unavoidable consequence of aging and the disability produced by the aging spine has emerged as a major health problem in the industrialized world. Alterations in the anatomical alignment and physiologic motion that normally exists between adjacent spinal vertebrae can cause significant pain, deformity, weakness, and catastrophic neurological dysfunction.

Surgical decompression of the neural tissues and immobilization of the vertebral bones is a common option for the treatment of spinal disease. Currently, vertebral fixation is most frequently accomplished by anchoring bone screws into the pedicle portion of each vertebral body and then connecting the various screw fasteners with an interconnecting rod. Subsequent rigid immobilization of the screw/rod construct produces rigid fixation of the attached bones.

The growing experience with spinal fusion has shed light on the long-term consequences of vertebral immobilization. It is now accepted that fusion of a specific spinal level will increase the load on, and the rate of degeneration of, the spinal segments immediately above and below the fused level. As the number of spinal fusion operations have increased, so have the number of patients who require extension of their fusion to the adjacent, degenerating levels. The rigidity of the spinal fixation method has been shown to correlate with the rate of the degenerative progression of the adjacent segments. In specific, implantation of stiffer instrumentation, such as rod/screw implants, produced a more rapid progression of the degeneration disease at the adjacent segment than use of a less stiff fixation implant.

An additional shortcoming of the traditional rod/screw implant is the large surgical dissection required to provide adequate exposure for instrumentation placement. The size of the dissection site produces unintended damage to the muscle layers and otherwise healthy tissues that surround the diseased spine. A less invasive spinal fixation implant would advantageously minimize the damage produced by the surgical exposure of the spine.

SUMMARY

The preceding discussion illustrates a continued need in the art for the development of a minimally invasive method of vertebral fixation of reduced rigidity.

In a first embodiment, there is disclosed an orthopedic device adapted to fixate the spinous processes of vertebral bones. The implant includes at least one bone engagement member located on each side of a spinous process and adapted to forcibly abut the side of each spinous process. The engagement member only abuts a single spinous process and does not abut another surface of a second spinous process. The implant further includes a connector member adapted to interconnect the bone engagement members on each side of a spinous processes. The connector member is defined by a long axis that is substantially longitudinal and parallel to the spinous processes. The implant further includes a connection between the bone engagement members and the connector member. The connection is capable of reversibly transitioning between a first state, wherein the orientation between the engagement member and the connector member is changeable in at least one plane and a second state, wherein the orientation between the engagement member and the connector member is rigidly affixed. The implant further includes a cross member extending across the vertebral midline and adapted to adjustably couple the longitudinal connector members that are located on each side of the vertebral midline. The cross member reversibly transitions between a first state, wherein the orientation between the longitudinal connector members and the cross member is changeable and a second state, wherein the orientation between the longitudinal connector members and the cross member is rigidly affixed.

In a second embodiment, there is disclosed an orthopedic device adapted to fixate the spinous processes of vertebral bones. The orthopedic device includes at least one bone engagement member located on each side of at least two adjacent spinous processes and adapted to forcibly abut the side of the spinous processes. The engagement member is substantially comprised of a contoured rod and contains at least one side aperture that permits contact between bone graft material and the spinous processes. The device further includes a cross member extending across the vertebral midline and adapted to adjustably couple the longitudinal bone engagement members that are located on each side of the vertebral midline. The cross member is capable of reversibly transitioning between a first state, wherein, the orientation between the longitudinal bone engagement members and the cross member is changeable in at least one plane and a second state, wherein the orientation between the longitudinal bone engagement members and the cross member is rigidly affixed In another embodiment, there is disclosed an orthopedic device adapted to fixate the spinous processes of vertebral bones. The device includes at least one bone engagement member located on each side of at least two adjacent spinous processes and adapted to forcibly abut the side of the spinous processes. The bone engagement member is substantially comprised of a plate that contains a curvilinear end surface adapted to engage a connecting member, wherein the curvilinear end surface is not located on a bone engaging surface of the plate. The device further includes a cross member extending across the vertebral midline and adapted to adjustably couple the longitudinal bone engagement members that are located on each side of the vertebral midline. The cross member has a complimentary surface adapted to engage the curvilinear end surfaces of the longitudinal bone engagement members and to provide a changeable attitude between them. The cross member is further adapted to reversibly transition between a first state, wherein the orientation between the longitudinal bone engagement members and the cross member is changeable in at least one plane and a second state, wherein the orientation between the longitudinal bone engagement members and the cross member is rigidly affixed.

In another embodiment, there is disclosed an orthopedic device adapted to fixate the spinous processes of the vertebral bones wherein the device is adapted to accepted an additional bone fastener that is placed into the base of the spinous process in a substantially horizontal trajectory.

Other features and advantages will be apparent from the following description of various embodiments, which illustrate, by way of example, the principles of the disclosed devices and methods.

BRIEF DESCRIPTION OF THE DRAWINGS

FIG. 1 shows perspective views of an exemplary embodiment of an orthopedic implant.

FIG. 2B illustrate multiple views of a locking member of the implant.

FIG. 3A shows a section of a locking mechanism of the implant in the locked and rigid position.

FIG. 3B shows a section of a locking mechanism of the implant in the un-locked and non-rigid position.

FIG. 4 shows a section of another locking mechanism of the implant.

FIG. 5A and FIG. 5B show a perspective view of the embodiment prior to screw placement and after screw placement, respectively.

FIG. 8 shows an alternative locking mechanism of the implant.

FIG. 12 shows the device of FIG. 11 in multiple orthogonal planes.

FIG. 13A shows an exploded view of the implant.

FIG. 13B illustrates a cross-sectional view of the locking mechanism.

FIGS. 19A and 19B show a locking mechanism between the modular attachment device of FIG. 17 and the device of FIG. 14. The locking mechanism is shown in the unlocked state in FIG. 19A and in the locked state in FIG. 19B.

DETAILED DESCRIPTION

Figure 2A:
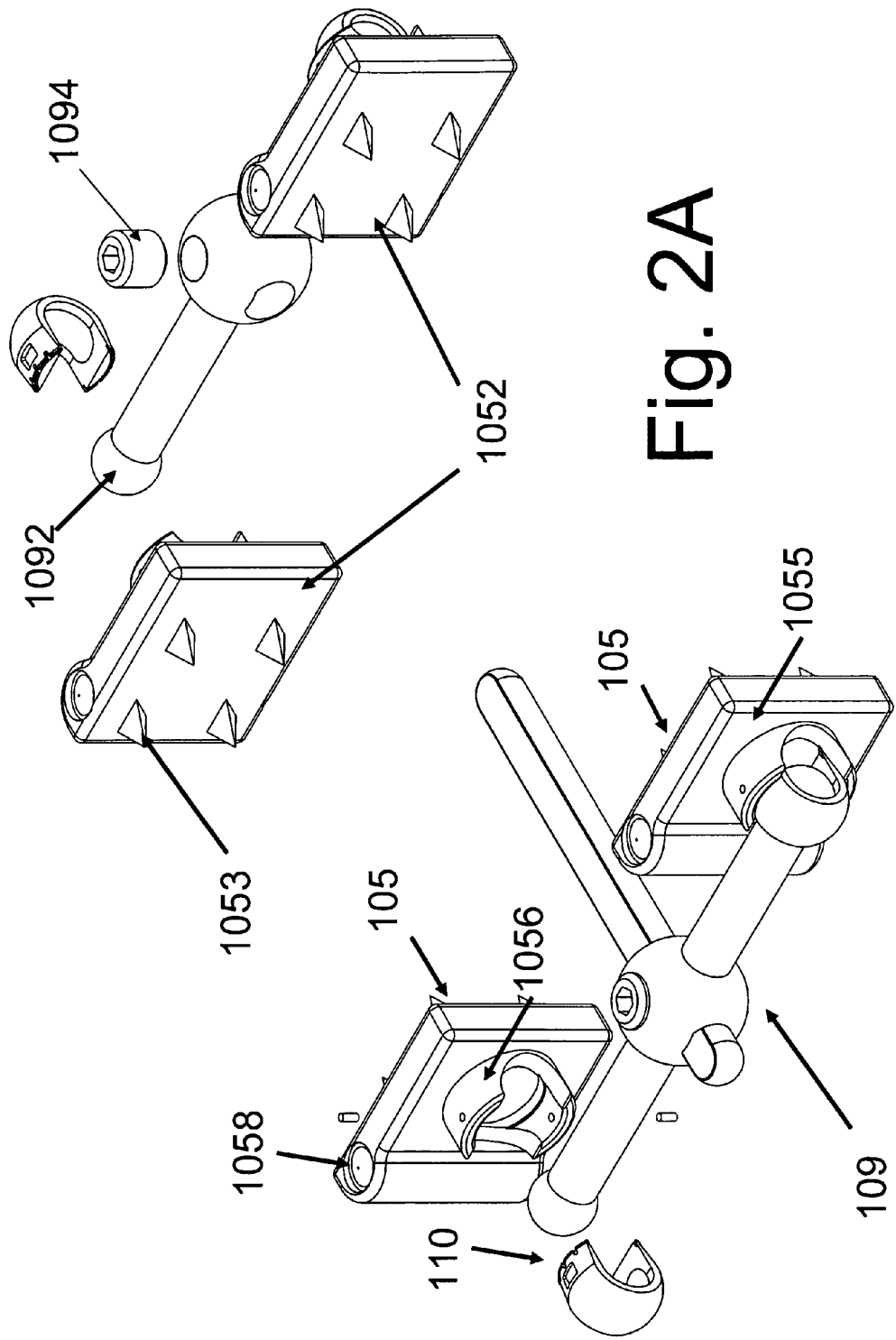
FIG. 2A shows an exploded view of the implant embodiment.

FIG. 1 shows a perspective view of an exemplary embodiment of a vertebral fixation implant. The implant can be anchored across multiple levels of vertebral bones via one or more spiked anchor members, such as members 105. For clarity of illustration, the device is shown attached to two adjacent vertebral bones. The vertebrae are represented schematically and those skilled in the art will appreciate that actual vertebral bones may include anatomical details that differ from those shown in FIG. 1. An exploded view of the implant is shown in FIG. 2A.

In a device intended to immobilize two vertebral bones, four anchor members 105 are interconnected by "H" shaped rod connector 109. The rod connector 109 includes a pair of rods that extend generally parallel to the vertebral midline and a single cross rod that crosses the vertebral midline. The cross rod interacts with a locking element that can be used to adjust the position of the cross rod relative to the pair of rods that extend generally parallel to the vertebral midline.

The rod connector interacts with a plurality of anchor members 105 that are positioned so that each can be affixed onto each side surface of a spinous process of each vertebra. The anchor member 105 is adapted to affix onto the side surface of the spinous process and can have various structures suited for such a purpose. In the illustrated embodiment, the anchor member contains an inner abutment surface 1052 that contains structures adapted to attach to the spinous process, such as spiked projections 1053. Each anchor member 105 also has an outer surface 1055 that contains a receptacle member 1056 adapted to receive a segment of rod connector 109. A locking member 110 (FIG. 2B) is adapted to interact with receptacle member 1056 and rigidly affix rod connector 109 onto an anchor member 105. As described below, the locking member 110 is sized and shaped to be positioned inside a central cavity of receptacle member and locked in place therein. Each anchor member 105 can optionally contain a bore hole 1058 that is adapted to accept a bone screw or other fastener that, when applied, can increase the fixation strength of the device onto bone.

Through its interaction with locking member 110, receptacle member 1056 of anchor member 105 is adapted to allow adjustable placement of rod connector 109 relative to member 105 and provide an adjustable orient for spike members 1053 relative to the spinous process. In use, the anchor members 105 are attached to the spinous processes by driving the spike members 1053 into the spinous processes. After each of two members 105 are forcibly driven into opposing sides of a spinous process of a single spinal vertebra, locking member 110 is compressed into the central cavity of receptacle member 1056. The locking member 110 interacts with the receptacle member 1056 and the rod connector 109 such that a segment of rod connector 109 is rigidly affixed within the receptacle member 1056. The locking member 110 is adapted to reversibly transition from a first un-locked state in which member 1056, member 110 and the interacting segment of rod connector 109 are movable to a second locked state wherein the device members are rigidly affixed to another, as described more fully below.

FIG. 2B shows various views of an exemplary embodiment of locking member 110. In the illustrated embodiment, locking member 110 has a spherical inner cavity 1102 adapted to accept a spherical end segment 1092 of connecting rod 109. Outer surface 1104 of locking member 110 is adapted to fit within and interact with a conical inner surface of receptacle member 1056 of anchor member 105. An outer wall relief 1109 is adapted to accept a retention pin. A second relief, 1106, is located on an open end of locking member 110 and allows the formation of deformable flap with protrusion tip 1108.

A cross-sectional view of the locking mechanism is shown in FIG. 3A (locked state) and in FIG. 3B (unlocked state). In the unlocked state shown in FIG. 3B, spherical end segment 1092 of connecting rod 109 is non-rigidly retained within cavity 1102 of member 110, permitting movement of connecting rod 109 relative to member 110 in one or more planes. With the application of a compressive load by a locking device (not shown), member 110 is forcibly advanced into the conical inner surface of receptacle member 1056. The advancement of locking member 110 into receptacle 1056 produces a centripetal force that rigidly immobilizes the connecting rod 109 to anchor member 105. The interaction of protrusion tip 1108 of locking member 110 with a relief on the inner wall of receptacle member 1056 (FIG. 3A) will maintain the construct in the locked position even after the locking instrument is removed.

While the inner cavity 1102 of member 110 can accept a spherical end segment 1092 of connecting rod 109, the flat surrounding segment 1103 of the inner aspect of member 110 can alternatively accommodate and interact with a cylindrical segment of rod 109. With member 110 in the unlocked position and a cylindrical segment of rod 109 engaged, member 110 can translate along the cylindrical segment of rod 109 and produce a device of variable length. In this configuration, rotational movement between segment 105 and interconnecting rod 109 occurs at the interface between member 110 and receptacle 1056 as well as within the second locking mechanism shown in FIG. 4.

A second locking mechanism can be used to maintain the device in a locked configuration. The second locking mechanism can be located within the rod connector 109 and actuated by the advancement of threaded screws 1094 into a complimentary threaded bore hole on connecting rod 109, as shown in FIG. 4. For clarity of illustration, the threads are not shown in FIG. 4. This second locking mechanism exerts a compressive load onto locking member 110 and maintains the device in the locked configuration. It also places a compressive load across each of the two anchor members 105 placed on apposing sides of a spinous process and keeps the spiked projections 1053 rigidly affixed to bone.

Figure 6:
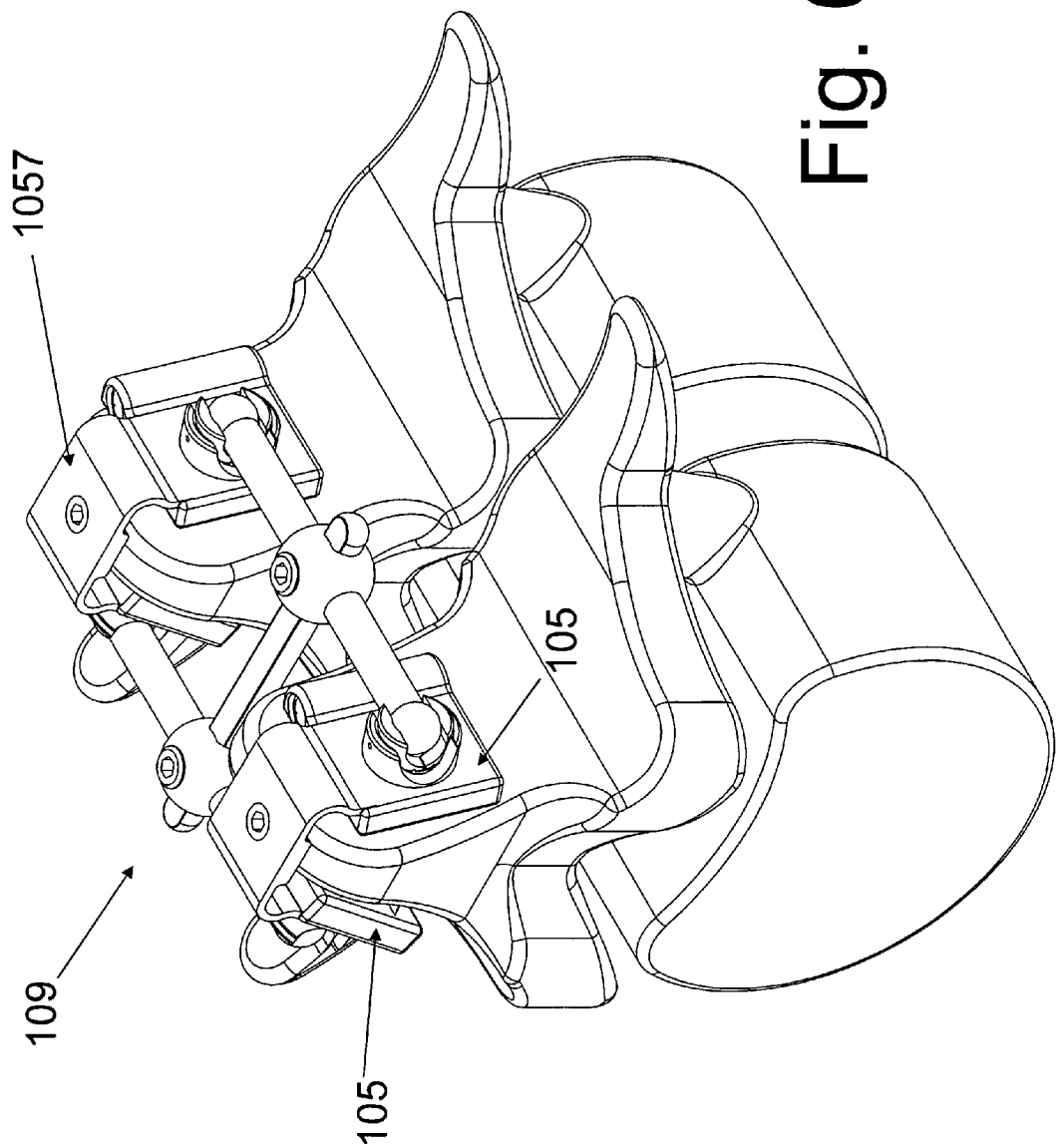
FIG. 6 shows a second embodiment of the implant attached to a vertebral bone model.
Figure 7A:
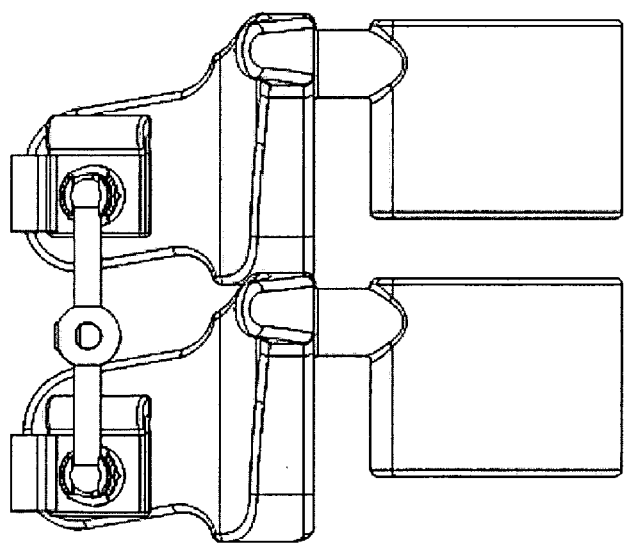
FIG. 7A shows a side perspective of the embodiment of FIG. 6.
Figure 7B:
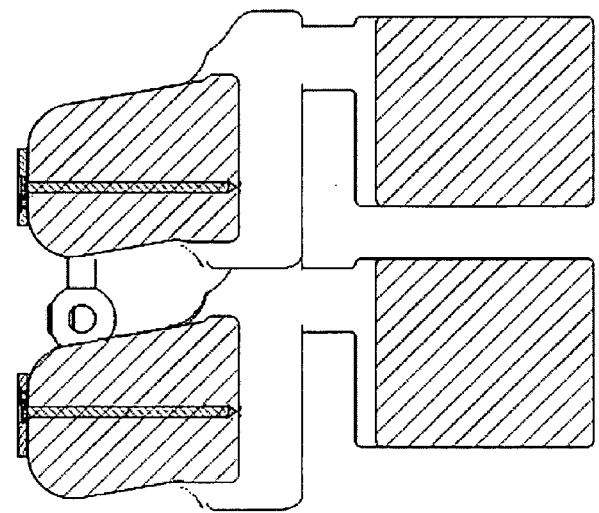
FIG. 7B shows a cross-sectional view of the device of FIG. 7A.

Bone fixation may be strengthened further by the placement of bone screws or similar fasteners through bore holes within the anchor members 105, such as bore hole 1058. The insertion of bone screws into the anchor members 105 is illustrated in FIGS. 5A and 5B. Bores 1058 are positioned in member 105 so as to provide a substantially axial (i.e., horizontal) screw trajectory and advance the distal screw segment into the base of the spinous process. Preferably, each of the two opposite screws anchored onto a single spinous process are adapted to follow a non-parallel trajectory so as to further enhance bone fixation. In addition, the screw top may be angled so as to provide a Morse-taper like fit within the bore hole 1058. Alternatively, a secondary feature may be added to lock the bone screw onto anchor member 105 after the screws are fully seated into the underlying bone. An additional tab 1057 may be used to connect two anchor members 105 across the midline of the spinous process. This variation is shown in FIG. 6, which shows the tab 1057 that extends over the spinous process. In an embodiment, the tab 1057 has malleable sides that permit relative motion between each anchor member 105. The tab 1057 may also contain a central bore that is adapted to accept a bone fastener anchored into the spinous process. FIG. 7A show a lateral view of the device of FIG. 6, while FIG. 7B illustrates a lateral cross sectional view that shows the bone screw extending along the long axis of the spinous process through the tab 1057.

Figure 9:
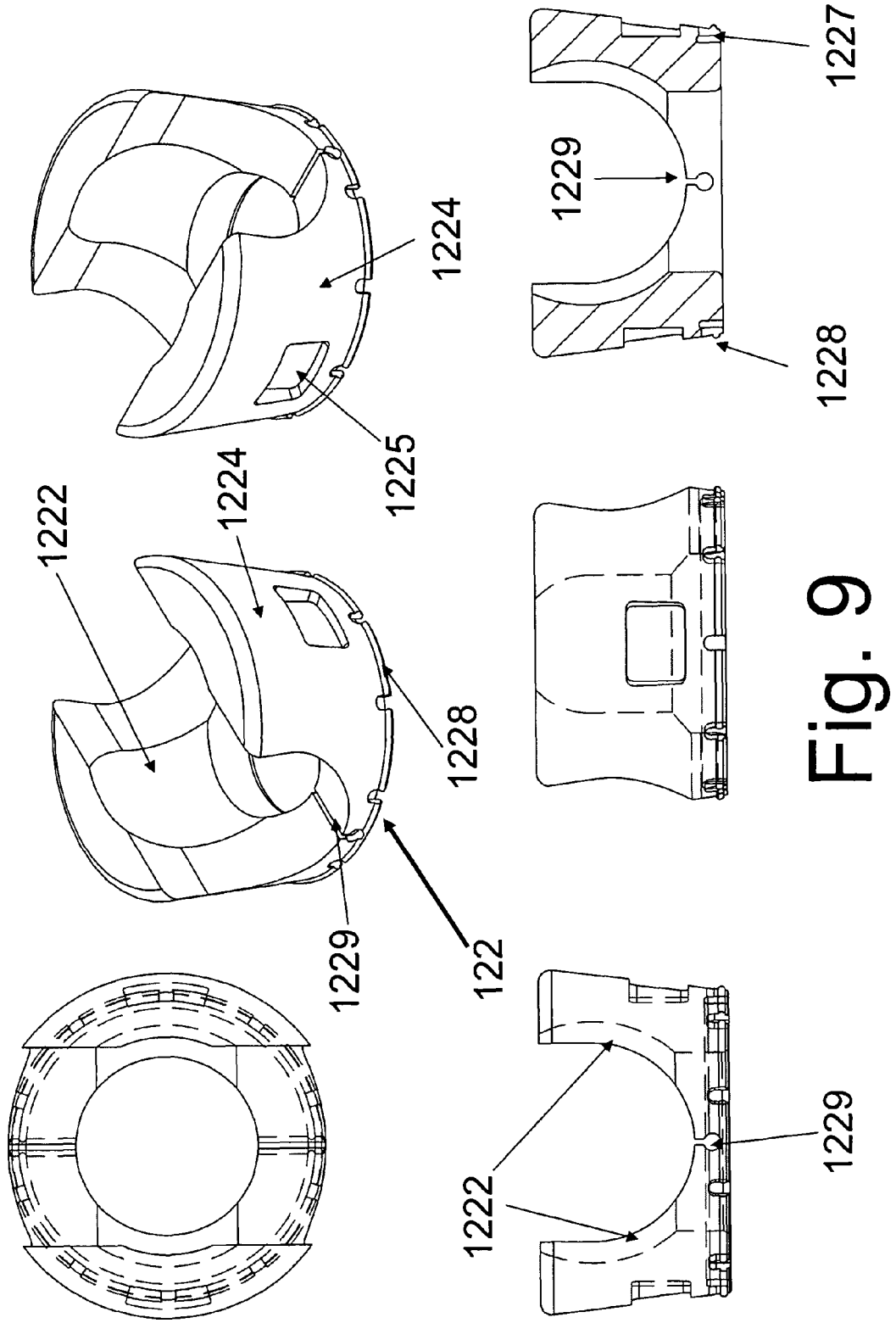
FIG. 9 shows a member of the alternative locking mechanism.
Figure 10:
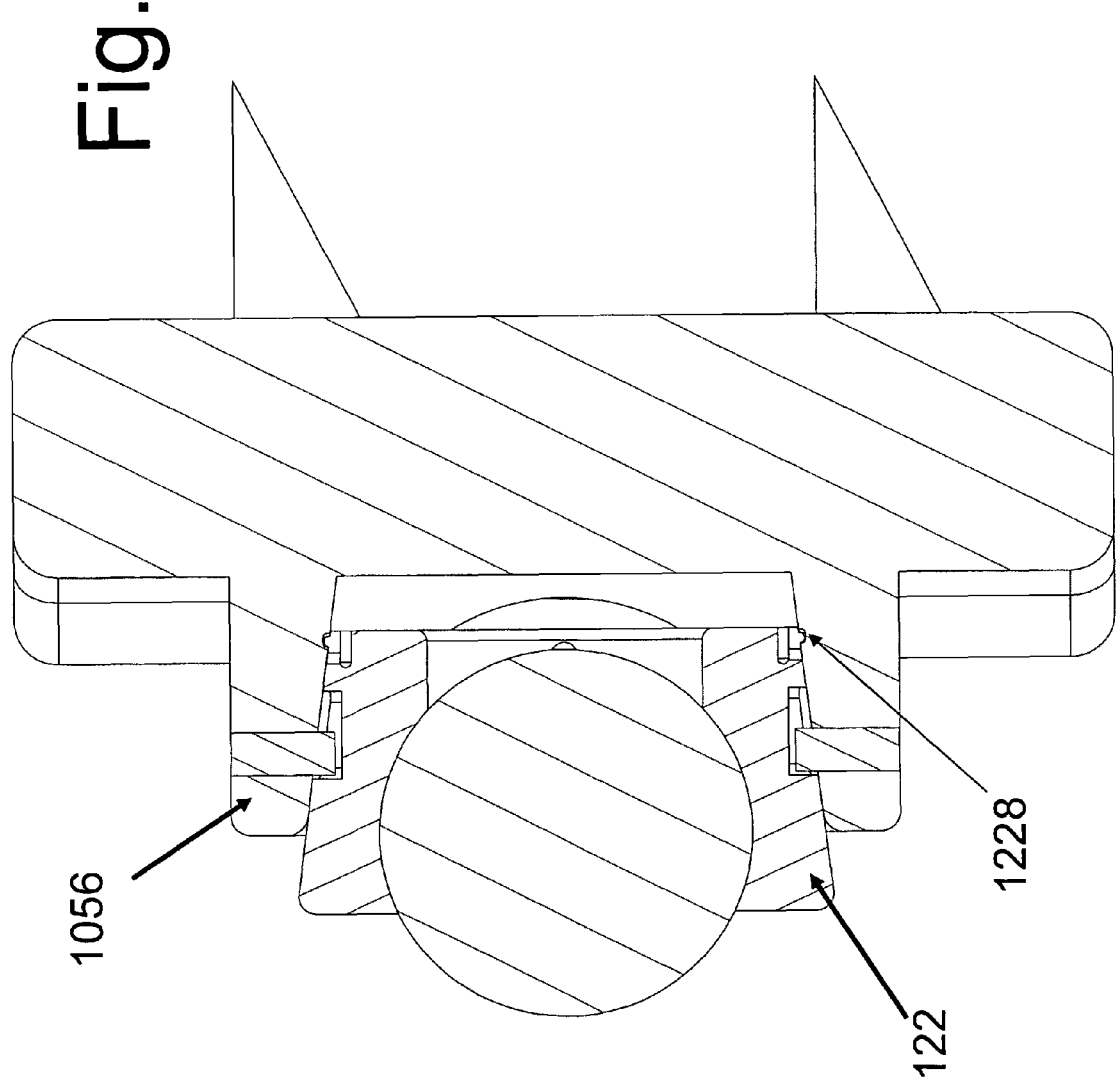
FIG. 10 illustrates a cross-sectional view of the alternative locking mechanism.

An alternative locking member that reversibly locks connecting rod 109 and receptacle 1056 of member 105 is shown in FIGS. 8 through 10. This embodiment has a modified version of the locking member, which is shown in FIG. 9. Locking member 122 has an inner cavity 1222 that is sized and shaped to accept spherical end 1092 of connecting rod 109. Member 122 has conical outer wall 1224 that fits within receptacle member 1056. Relief 1225 of wall 1224 is adapted to accept a retention pin. Another relief, 1227, is located on the inferior surface of locking member 122 and allows the formation of deformable flap with protrusion tip 1228. A key hole relief 1229 allows the superior aspect of member 122 to angle inward in response to a compressive load and constrict inner cavity 1222 of the locking member 122.

A cross-sectional view of the alternate embodiment of the locking mechanism is shown in FIG. 10 in the locked configuration. With the application of a compressive load by a locking device (not shown), member 122 is forcibly advanced into the conical inner surface of receptacle member 1056. Because of the difference in wall angle between the outer wall of member 122 and the inner wall of receptacle 1056, advancement of member 122 into receptacle 1056 produces a centripetal inclination of the walls of member 122 and rigidly immobilizes the connecting rod 109 to anchor member 105. The interaction of protrusion tip 1228 of locking member 122 with a relief on the inner wall of receptacle member 1056 will maintain the construct in the locked position even after the locking instrument is removed. As previously discussed with reference to member 110, a cylindrical segment of connector rod 109 may be alternatively used to interact with member 122 and produce a device of variable length.

The device may be also used to fixate more than two vertebral levels. In this procedure, the total length from the top-most to lower-most spinous process is measured and the number of spinous processes to be affixed is counted. An interconnecting longitudinal rod of the appropriate length is selected and coupled with the appropriate number of bone anchor members 105. Either one, both or none of the longitudinal interconnecting rod ends may be spherical. Members 110 of the anchor member 105 will couple and interaction with cylindrical portion of the longitudinal rod to provide an adjustable spacing between members 105. An interconnecting rod with the appropriate number of member 105 is placed on each side of the midline.

Starting at a selected level, a locking compression device (not shown) is used to drive the spikes of the members 105 into each side of the spinous process. The locking compression device is left in position and the procedure is repeated onto the next spinous process level. Prior to the rigid fixation of member 110 within receptacle 1056, the attitude of member 105 may be adjusted by rotation and translation relative to the interconnecting rod. After anchoring the opposing member 105 into the spinous process, the locking device is left in place and the procedure is sequentially moved to another level. After fixation of a number of levels has been accomplished, the surgeon can place a cross member across the midline and couple each of the longitudinal rods. This step can be performed after some or all members 105 have been rigidly affixed to their designated vertebral level. After cross member placement, the locking compression device attached to each secured level is removed. If desired, an additional bone screw fastener may be placed through bore hole 1058.

Figure 11:
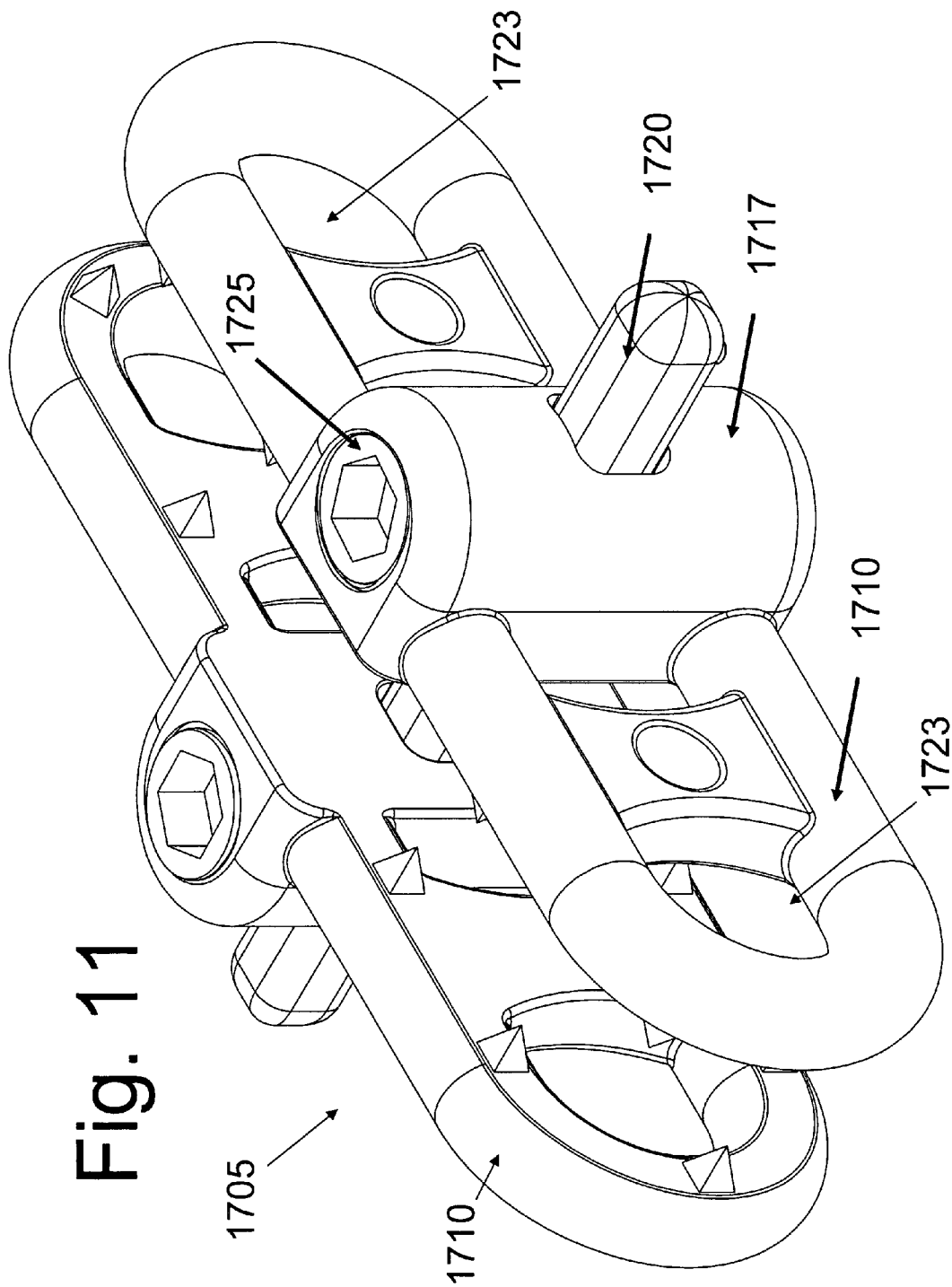
FIG. 11 illustrates a perspective view of another embodiment of an orthopedic implant.

FIGS. 11 through 13 illustrate an additional device embodiment. A perspective view is shown in FIG. 11 while multiple orthogonal views are illustrated in FIG. 12. The device 1705 is comprised of two bone engaging members 1710 that are each formed of a pair of contoured or curved rods that extend outwardly from a central member 1717. The bone engaging members 1710 are separated by a space that is sized and shaped to receive a bone structure, such as the spinous process of a vertebral body. Opposed surfaces of the bone engaging members 1710 have attachment means such as spikes, knurls or other protrusions on the bone-facing aspect of each bone-engaging member. An interconnecting member 1720 comprised of an elongated rod is adapted to extend through a fitted bore hole within each central member 1717. A locking screw 1725 is adapted to reversibly lock a segment of interconnecting member 1720 within each central member 1717.

FIG. 13A shows an exploded view of the device. FIG. 13B illustrates a cross-sectional view through the locking mechanism. Central member 1717 has a central bore 1728 along and the long access that is adapted to accept locking screw 1725 and a second bore 1730 that is adapted to accept interconnecting ember 1720. Compressible spherical member 1732 has bore hole 1734 and open side notch 1735. As shown in FIG. 13B, member 1732 is contained within bore hole 1728 of central member 1717 and surrounds a segment of interconnecting member 1720 in the assembled device. Locking screw 1725 abuts a surface of compressible spherical member 1732. In the unlocked state, interconnecting member 1720 is freely movable within member 1732. Spherical member 1732 can also rotate within central hole 1728, thereby proving an adjustable relationship between each bone engaging members 1710 and interconnecting rod 1720. With advancement of locking screw 1725, spherical member 1732 is forcibly compressed onto rod 1720 and immobilized within central hole 1728, thereby locking interconnecting rod 1720 within bone engaging member 1710.

In placement of the device onto bone, each bone engaging member 1710 is situated on an opposite side of the spinous processes to be immobilized. A compressive force is applied by a locking instrument (not shown) across members 1710 so as to drive the spikes into the side of the spinous processes of neighboring vertebrae and immobilize them. The interconnecting member 1720 is used to maintain compression even after the locking instrument has been removed. In this regard, the threaded locking screws 1725 are advanced to provide a locked engagement between interconnecting member 1720 and each member 1710. After implantation, multiple apertures 1723 exist in this rod-based device that advantageously permit access to the underlying bone of the spinous processes. Bone graft material can be placed through apertures 1723 and into contact with the spinous processes in order to form and augment the bone fusion mass.

Figure 14:
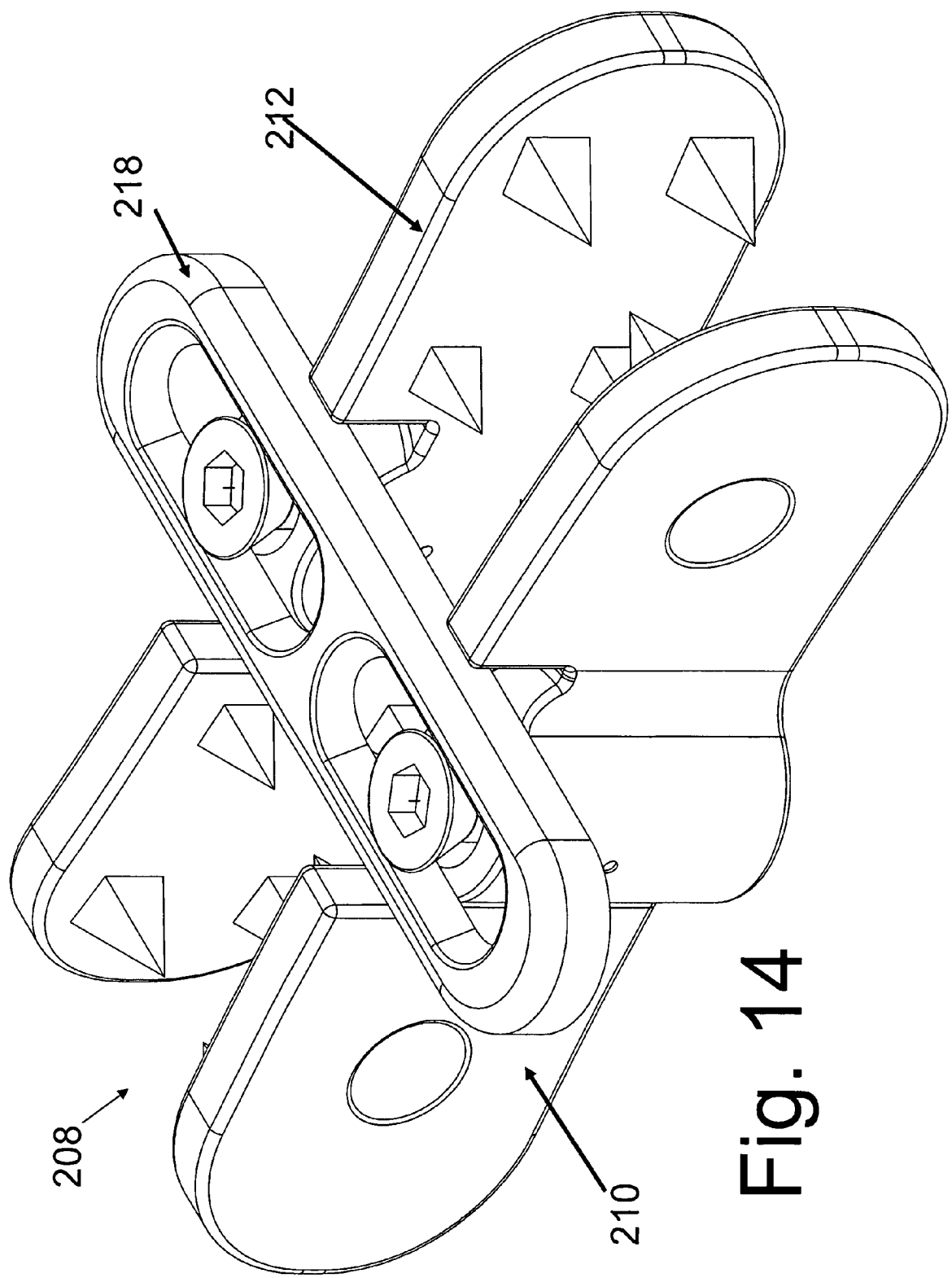
FIG. 14 shows a perspective view of another embodiment of an orthopedic implant.
Figure 15:
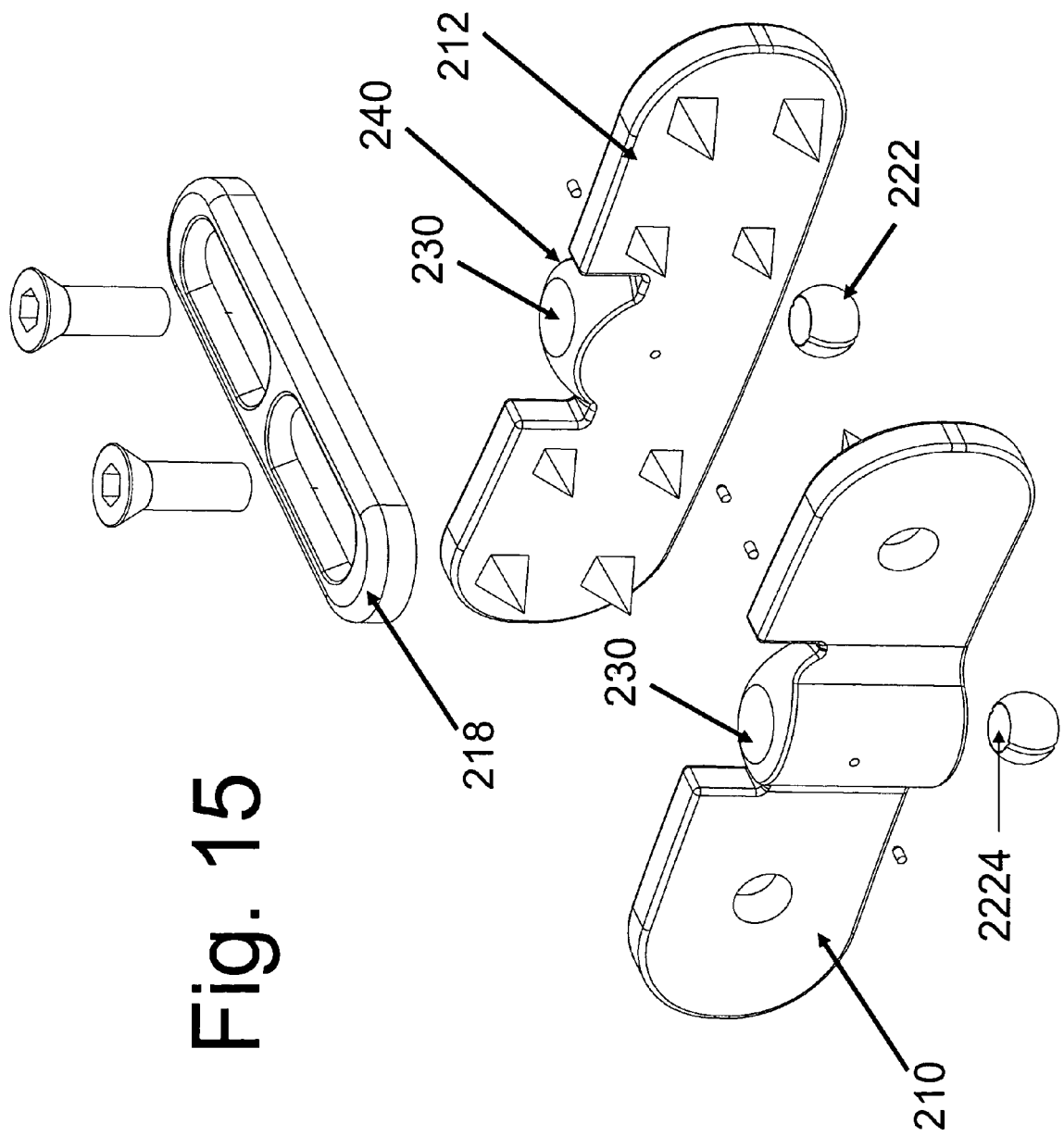
FIG. 15 shows an exploded view of the implant in FIG. 14.
Figure 16:
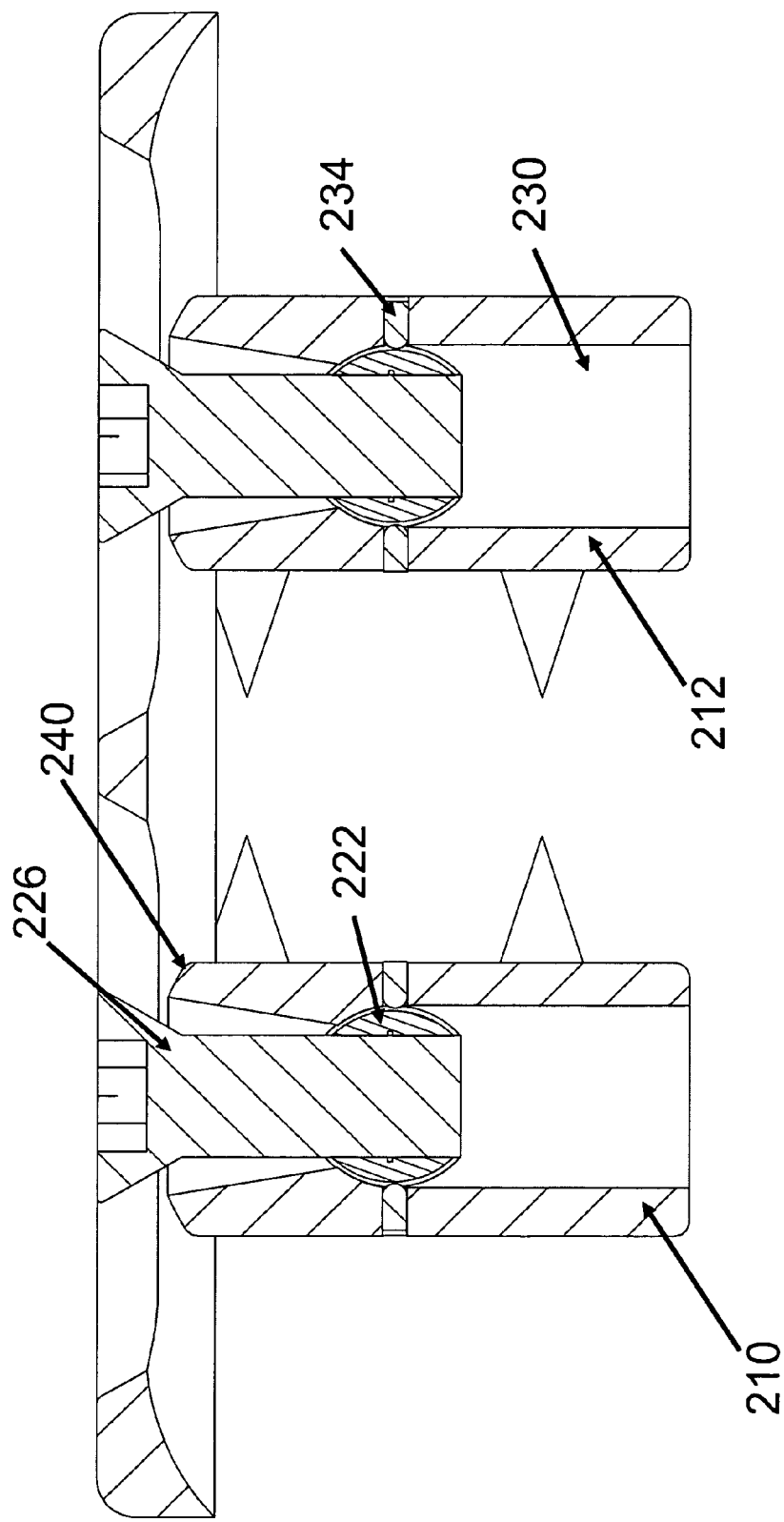
FIG. 16 shows a cross-section view of the locking mechanism of the implant embodiment of FIG. 14.

FIGS. 14 through 16 illustrate an additional device embodiment. A perspective view is shown in FIG. 14 while an exploded view in shown in FIG. 15. The device 208 is comprised of two bone engaging members 210 and 212 that are opposed to one another. The bone engaging members 210 and 212 are separated by a space that is sized and shaped to receive a bone structure, such as the spinous process of a vertebral body. Opposed surfaces of the bone engaging members 210 and 212 have attachment means such as spikes, knurls or other protrusions on the bone-facing aspect of each bone-engaging member. In application, each member is situated on an opposite side of the spinous processes to be immobilized. A compressive force is applied by a locking instrument (not shown) across members 210 and 212 so as to drive the spikes into the side of the spinous processes of neighboring vertebrae and immobilize them. A slotted interconnecting plate 218 is used to maintain compression even after the locking instrument has been removed.

A cross-sectional view of the implant's locking mechanism is shown in the locked position in FIG. 16. A spherical member 222 has threaded central bore 2224 and accepts threaded screw 226 (threads not shown for either member). Member 222 resides within bores 230 (FIG. 15) of plate members 210 and 212. Bore 230 is adapted to permit insertion of member 222 from the bottom. A securement member, such as a protrusion within bore 230, prevents member 222 from emerging from the top. Retention pins 234 retain member 222 within bore 230 and prevent its rotation relative to long axis of bore 230. The top surface of each member 210 and 212 contains a spherical protrusion 240 that has the same center of rotation as seated member 222. The inferior surface of interconnecting plate 218 has a complimentary spherical indentation that compliments the spherical surface protrusion 240 of members 210 and 212. In this way, each member 210 and 212 can be independently oriented relative to interconnecting plate 218. With advancement of threaded screw 226 into member 222, the interconnecting plate 218 is locked relative to members 210 and 212.

Figure 17:
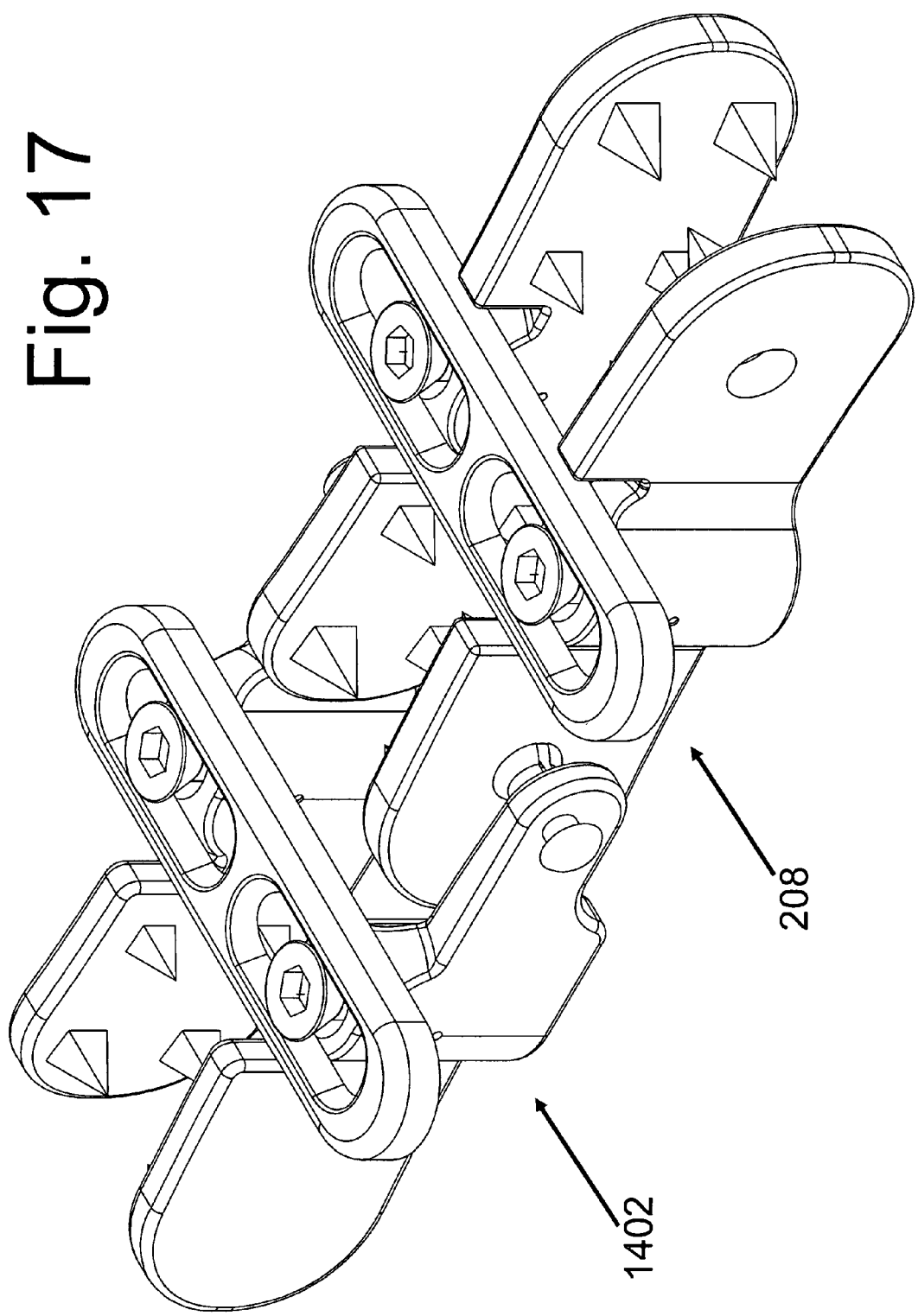
FIG. 17 shows a modular attachment device.
Figure 18:
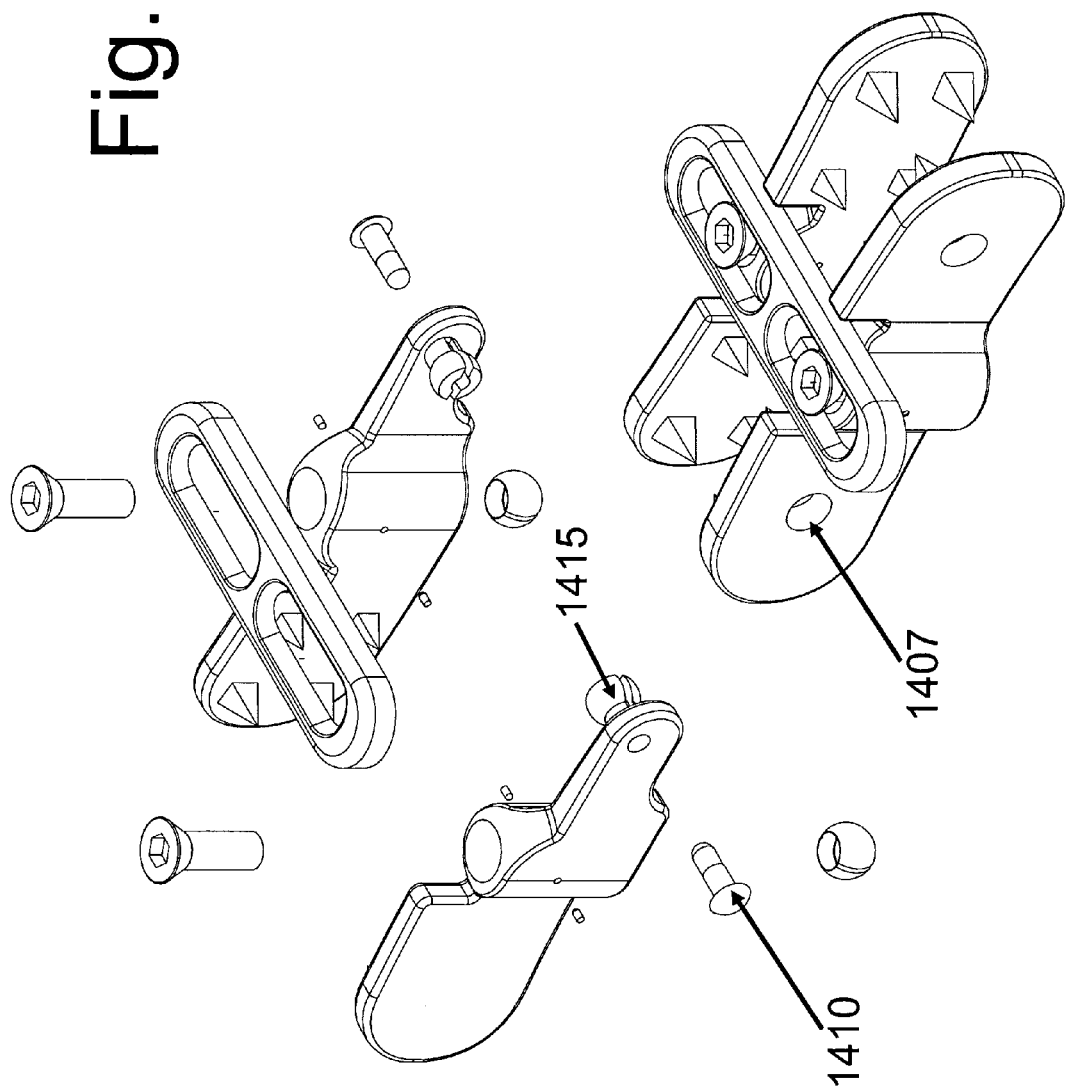
FIG. 18 illustrates an exploded view of the modular attachment device of FIG. 17.

A modular device 1402 is shown in FIGS. 17 through 19. The modular device is adapted to reversibly lock onto an implanted device 208 and thereby extend the affixing of an adjacent vertebral body to the implanted device 208. FIG. 17 shows the modular device attached to an implanted device 208. FIG. 18 shows the modular device in an exploded state adjacent to an assembled device 208, which is substantially identical or similar to the device shown in FIGS. 14-16. A locking mechanism 1405 is adapted to reversibly lock onto the device 208 by interacting with a hole 1407 in the device 208. The locking mechanism 1405 includes a pin 1410 that fits into an expandable head 1415 that is positionable within the hole 1407.

FIG. 19A shows the locking mechanism 1405 in a unlocked state with the device 208. The pin 1410 is partially positioned within the expandable head 1415, which is located inside bore 1407 of the bone engaging member 210. Member 210 has a curved inner surface that is adapted to interact with the complimentary outer surface of head 1415 and permit movement therebetween. With the pin 1410 in the unlocked position shown in FIG. 19A, modular device 1402 and member 210 are movable relative to one another in one or more planes. FIG. 19B shows the locking mechanism 1405 in a locked state such that the pin 1410 has been fully inserted into the expandable head 1415. This has caused the head 1415 to expand outward within bore hole 1407 and provide an interfering, locked engagement between the modular device and the bone engaging member 210. The two devices are thus locked relative to one another.

Figure 20:
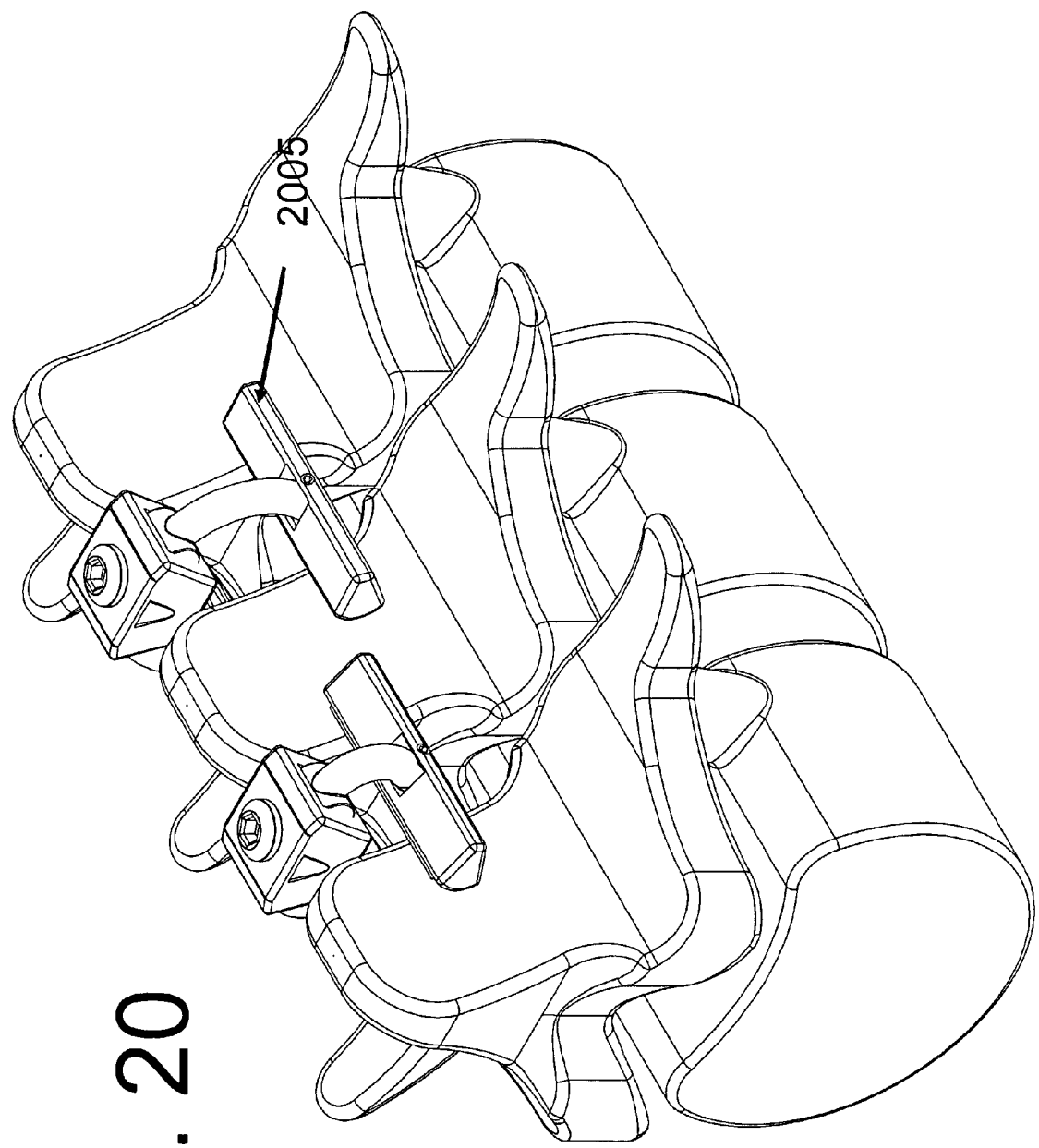
FIG. 20 shows a perspective view of another embodiment attached to vertebral bones.
Figure 21:
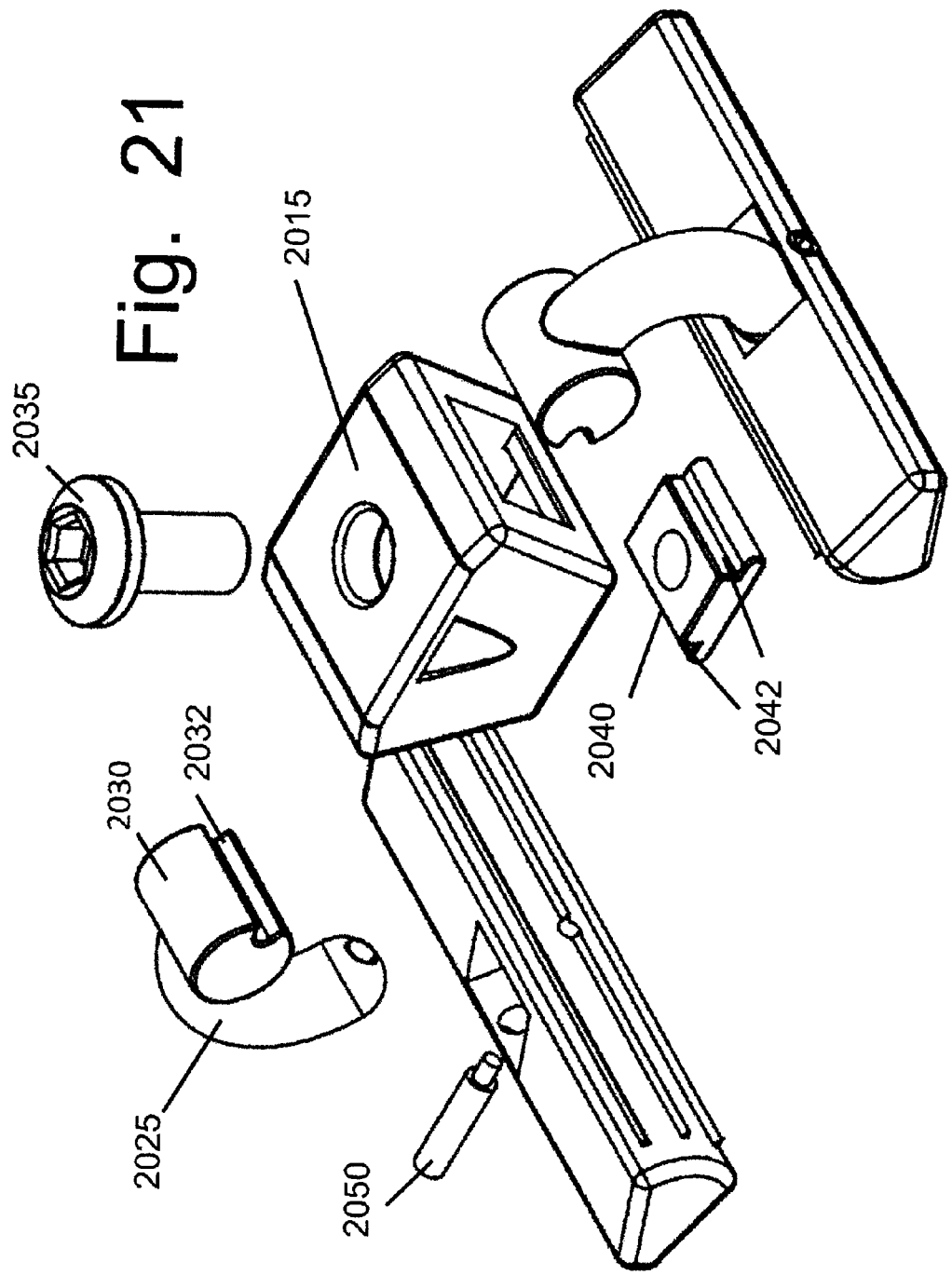
FIG. 21 illustrates the device of FIG. 20 in an exploded view.
Figure 22:
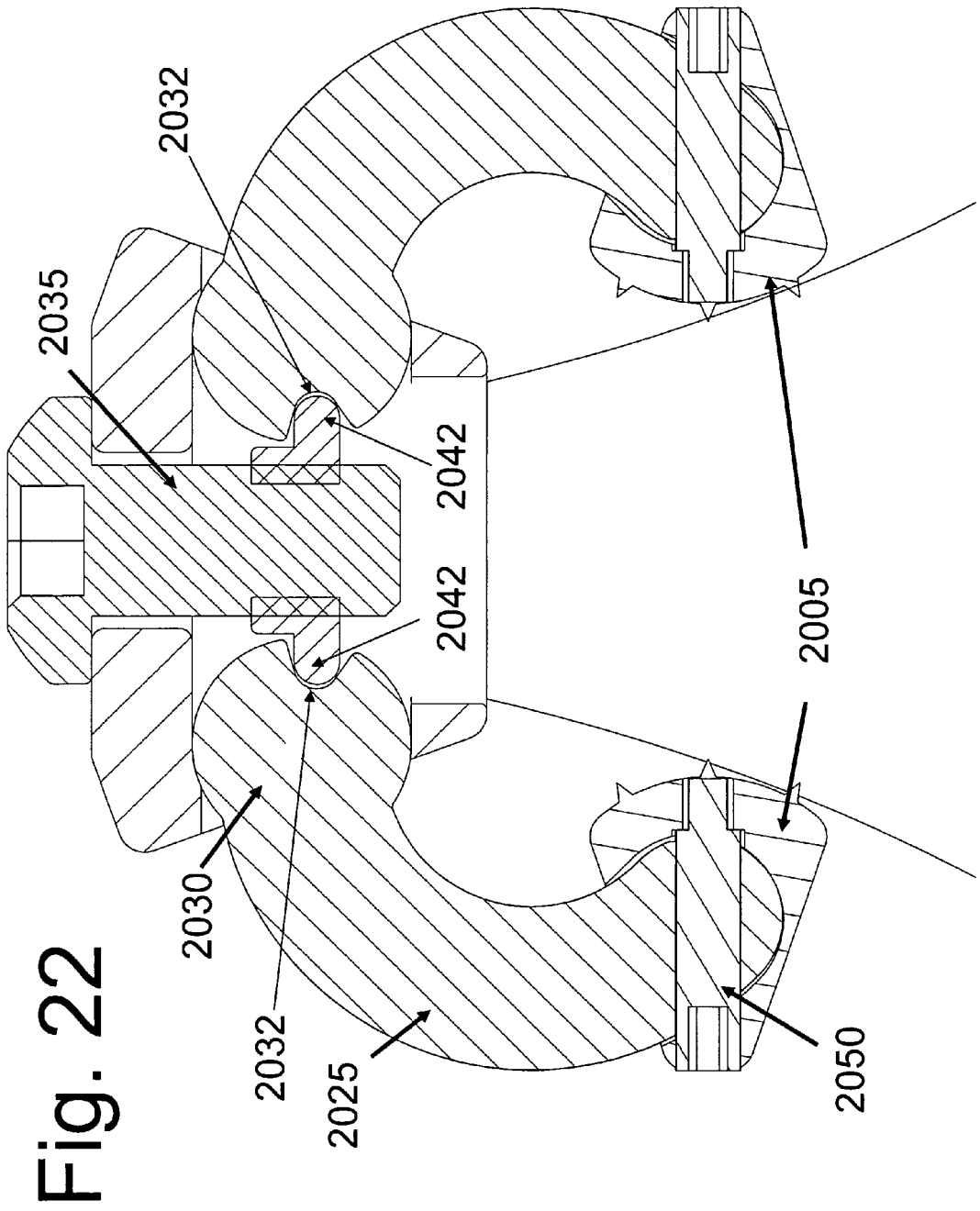
FIG. 22 shows a cross-sectional view through the locking mechanism of the device.

FIGS. 20 through 22 illustrate an additional device embodiment. FIG. 20 shows the device attached to vertebral bones and FIG. 21 shows the device in an exploded state. The device is comprised of two bone engaging members 2005 formed of elongated rods configures to be positioned adjacent the vertebral bodies. The bone engaging members 2005 are separated by a space that is sized and shaped to receive a bone structure, such as the spinous process of a vertebral body. Opposed surfaces of the bone engaging members 2005 have attachment means such as spikes, knurls or other protrusions on the bone-facing aspect of each bone-engaging member.

With reference to FIG. 20-22, the bone engaging members 2005 are connected to a central member 2015 by a pair of curved connecting arms 2025 with enlarged heads 2030. The connecting arms 2025 and the bone engaging members 2005 are joined together by retention pins 2050. The heads 2030 can pivot inside the cavity of central member 2015 such that the bone engaging members 2005 can move toward and away from the spinous processes.

A threaded locking screw 2035 engages threaded locking nut 2040 within the central cavity of central member 2015. Edges 2042 of member 2040 are contained within indentions 2032 of heads 2030. As locking screw 2035 is rotated and locking nut is moved towards the head 2037 of screw 2035, heads 2030 of connecting arms 2025 are rotated within the central cavity of member 2015. Rotation of heads 2030 cause the bone engaging members 2005 to pivot inward by virtue of the curved shape of the connecting arms 2025. The bone engaging members 2005 thereby are caused to exert a compressive force onto the spinous processes and to be secured thereto. Conversely, rotation of the locking 2035 in the reverse direction will cause the bone engaging member 2005 to move away from the spinous processes.

The disclosed devices or any of their components can be made of any biologically adaptable or compatible materials. Materials considered acceptable for biological implantation are well known and include, but are not limited to, stainless steel, titanium, tantalum, shape memory alloys, combination metallic alloys, various plastics, resins, ceramics, biologically absorbable materials and the like. Any components may be also coated/made with osteo-conductive (such as deminerized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components can also be entirely or partially made of a shape memory material or other deformable material.

Although embodiments of various methods and devices are described herein in detail with reference to certain versions, it should be appreciated that other versions, embodiments, methods of use, and combinations thereof are also possible. Therefore the spirit and scope of the appended claims should not be strictly limited to the description of the embodiments contained herein.

The invention claimed is:

1. A method for the fixation of a first vertebral bone to at least a second vertebral bone, comprising:
    providing an orthopedic implant, comprising:
        at least four bone abutment surfaces, a first abutment surface configured to attach to a second abutment surface via a first interconnecting member, a third abutment surface configured to attach to a fourth abutment surface via a second interconnecting member, the first and third bone abutment surfaces being aligned to face one another, and the second and fourth bone abutment surfaces being aligned to face one another;
        the first bone abutment surface being movably joined to the first interconnecting member via a coupling, the coupling being comprised of a first surface at least partially positioned within a conical inner surface of a receiving seat, the application of a locking force onto the coupling immobilizing the first bone abutment surface relative to the first interconnecting member, the components needed to immobilize the first interconnecting member being separated from threaded engagement, and the first bone abutment surface and the first interconnecting member configured to remain immobilized after removal of the locking force;
        a third interconnecting member configured to movably couple the first and the second interconnecting members, a locking mechanism being disposed at an intersection of the third interconnecting member and the first interconnecting member, and the locking mechanism being configured to transition into a configuration that limits movement between the third interconnecting member and the first interconnecting member;
    positioning the implant onto a posterior aspect of the first vertebral bone, the first bone abutment surface being positioned on a first side of a spinous process of the first vertebral bone, the third bone abutment surface being positioned on a second side of the spinous process of the first vertebral bone, and the first and the third bone abutment surfaces being aligned to face one another;
    positioning the implant onto the posterior aspect of the second vertebral bone, the second bone abutment surface being positioned on a first side of a spinous process of the second vertebral bone, the fourth bone abutment surface being positioned on a second side of the spinous process of the second vertebral bone, and the second and the fourth bone abutment surfaces being aligned to face one another;
    applying a force onto the implant, the force urging the first bone abutment surface towards the third bone abutment surface and capturing the spinous process of the first vertebral bone there between;
    rigidly affixing the first and second abutment surfaces to the first interconnecting member and the third and fourth abutment surfaces to the second interconnecting member; and
    actuating the locking mechanism that is positioned at the intersection of the first and the third interconnecting members, the actuated locking mechanism limiting movement between the first and third interconnecting members.

2. A method as in claim 1, wherein the force applied to urge the first bone abutment surface towards the third bone abutment surface is provided via a separate locking instrument.

3. A method as in claim 1, wherein a locking feature is disposed at a region of attachment between the second bone abutment surface and the first interconnecting member, and wherein the locking feature is configured to limit movement between the second bone abutment surface and the first interconnecting member.

4. A method as in claim 1, wherein a locking feature is disposed at a region of attachment between the third bone abutment surface and the second interconnecting member, and wherein the locking feature is configured to limit movement between the third bone abutment surface and the second interconnecting member.

5. A method as in claim 1, wherein a locking feature is disposed at a region of attachment between the fourth bone abutment surface and the second interconnecting member, and wherein the locking feature is configured to limit movement between the fourth bone abutment surface and the second interconnecting member.

6. A method as in claim 1, wherein the first surface of the coupling comprises at least a segment of a sphere.

7. A method as in claim 1, wherein a second coupling is configured to join the third bone abutment surface and the second interconnecting member, the second coupling comprising at least a surface member configured to wedge within a receiving seat member.

8. A method as in claim 1, wherein a second coupling is configured to join the fourth bone abutment surface and the second interconnecting member, and wherein the second coupling is comprised of at least a surface member configured to wedge within a receiving seat.

9. A method as in claim 1, wherein the implant comprises at least one bone fixation member and is configured to immobilize three or more bones relative to one another.

10. A method as in claim 1, wherein at least one of the first and second bone abutment surfaces comprises a tapered projection configured to penetrate bone.

11. A method as in claim 1, wherein at least one of the third and fourth bone abutment surfaces comprises a tapered projection configured to penetrate bone.

12. A method as in claim 1, further comprising first and second bone abutment surfaces being separated by a variable distance along a direction of the first interconnecting member.

13. An orthopedic implant configured to attach onto at least a first bone and a second bone, comprising:
 a first bone abutment member movably joined to a first interconnecting member via a coupling, the coupling comprising a first surface of one of the first bone abutment member or the first interconnecting member and a receiving seat of the other of the first bone abutment member or the first interconnecting member, the first surface being at least partially contained within a conical inner surface of the receiving seat;
 the coupling comprises a locking feature that is devoid of threaded engagement and configured to transition from a first state to a second state via application of a locking force, in the second state, the locking feature is configured to limit movement between the first bone abutment member and the first interconnecting member, the locking feature is further configured to remain in the second state after removal of the locking force;
 at least a second, third and fourth bone abutment members, the second bone abutment member being coupled to the first interconnecting member, the third bone abutment member and the fourth bone abutment member being jointly coupled via a second interconnecting member, the first and the third bone abutment members being aligned to face one another, and the second and fourth bone abutment members being aligned to face one another; and
 a third interconnecting member configured to couple the first and the second interconnecting members, a locking mechanism being disposed at an intersection of the first and third interconnecting members, and configured to limit movement between the first and the third interconnecting members in at least one plane.

14. An orthopedic implant as in claim 13, wherein the first bone abutment member comprises the conical seat of the coupling member.

15. An orthopedic implant as in claim 13, wherein the first bone abutment member and the second bone abutment member are separated by a variable distance along a length of the interconnecting member.

16. An orthopedic implant as in claim 13, wherein the first interconnecting member comprises at least a rod.

17. An orthopedic implant as in claim 13, wherein the implant comprises a retention pin configured to maintain the coupling in an assembled configuration.

18. An orthopedic implant as in claim 13, wherein the implant comprises a deflectable member configured to be in a first configuration when the locking feature is in the first state, and in a second configuration when the locking feature is in the second state.

19. An orthopedic implant as in claim 13, wherein the first bone abutment member is movable relative to the first interconnecting member in more than one plane.

20. An orthopedic implant as in claim 13, wherein the first bone abutment member comprises one or more surface projections configured to anchor onto bone.

21. An orthopedic implant as in claim 20, wherein at least one surface projection of the first bone abutment member comprises a tapered tip configured to penetrate into bone.

22. An orthopedic implant as in claim 13, wherein the implant comprises at least one bone fixation member and is configured to immobilize three or more bones relative to one another.

23. An orthopedic implant as in claim 13, wherein the second bone abutment member comprises a first surface and a second surface, the first surface comprising projections configured to anchor onto bone, and the second surface configured to couple with the first interconnecting member.

24. An orthopedic implant as in claim 13, wherein the second bone abutment member is movably joined to the first interconnecting member via a coupling that comprises a locking feature.

25. An orthopedic implant as in claim 13, wherein the third bone abutment member is movably joined to the second interconnecting member via a coupling that comprises a locking mechanism, the locking mechanism configured to transition from a first state to a second state, the locking mechanism configured to permit movement between the second interconnecting member and the third bone abutment member when the locking mechanism is in the first state, the locking mechanism configured to limit movement between the second interconnecting member and the third bone abutment member when the locking mechanism is in the second state.

26. An orthopedic implant as in claim 13, wherein the fourth bone abutment member is movably joined to the second interconnecting member via a coupling.

27. An orthopedic implant as in claim 13, wherein a first segment of the first interconnecting member is configured to couple to the first bone abutment member, a second segment of the first interconnecting member is configured to couple to the second bone abutment member, a third segment of the first interconnecting member is configured to couple to the third interconnecting member, and the third segment is positioned between the first and the second segments of the first interconnecting member.

28. An orthopedic implant as in claim 13, wherein a first segment of the second interconnecting member is configured to couple to the third bone abutment member, a second segment of the second interconnecting member is configured to couple to the fourth bone abutment member, a third segment of the second interconnecting member is configured to couple to the third interconnecting member, and the third segment is positioned between the first and the second segments of the second interconnecting member.

29. An orthopedic implant as in claim 13, wherein the implant is at least partially comprised of a plastic material.

30. An orthopedic implant as in claim 13, wherein the implant is at least partially comprised of a metallic alloy.

31. An orthopedic implant as in claim 30, wherein the metallic alloy is at least partially comprised of Titanium.

32. An orthopedic implant as in claim 13, wherein the implant comprises a bioactive material configured to promote bone formation.

33. An orthopedic implant as in claim 13, wherein the implant comprises at least one bore hole configured to accept a bone fastener, the bone fastener configured to anchor onto the first or the second bones.

34. An orthopedic implant configured to attach onto at least a first bone and a second bone, comprising:
at least four bone abutment surfaces, a first abutment surface attached to a second abutment surface via a first interconnecting member and not facing one another, a third abutment surface attached to a fourth abutment surface via a second interconnecting member and not facing one another, the first and third bone abutment surfaces being aligned to face one another, the second and fourth bone abutment surfaces being aligned to face one another, and each of the abutment surface configured to be immobilized relative to the interconnecting member to which it is attached;
the first bone abutment surface being movably joined to the first interconnecting member via a coupling, the coupling comprising a first surface at least partially positioned within a conical inner surface of a receiving seat, the application of a locking force onto the coupling immobilizes the first bone abutment surface onto the first interconnecting member, the components needed to immobilize the first bone abutment surface on to the first interconnecting member being separated from threaded engagement, and the first bone abutment surface and first interconnecting member configured to remain immobilized after removal of the locking force; and
a third interconnecting member configured to movably couple the first and the second interconnecting members, a locking mechanism is disposed at an intersection of the third interconnecting member and the first interconnecting member, the locking mechanism configured to transition to a configuration that limits movement between the third interconnecting member and the first interconnecting member.

35. An orthopedic implant as in claim 34, wherein the first interconnecting member comprises at least a rod.

36. An orthopedic implant as in claim 34, wherein the first bone abutment surface and the second bone abutment surface are separated by a variable distance along a length of the first interconnecting member.

37. An orthopedic implant as in claim 34, wherein the implant comprises at least one bone fixation member and is configured to immobilize three or more bones relative to one another.

38. An orthopedic implant as in claim 34, wherein the coupling comprises a deflectable member configured to be in a first configuration when the first bone abutment surface is movable relative to the first interconnecting member, and in a second configuration when the first bone abutment surface is immobilized to the first interconnecting member.

39. An orthopedic implant as in claim 34, wherein at least one bone abutment surface comprises surface projections configured to anchor onto bone.

40. An orthopedic implant as in claim 34, wherein the second bone abutment surface is movably joined to the first interconnecting member by a coupling that comprises a locking feature, the locking feature configured to transition from a first state to a second state, when in the first state, the locking feature configured to permit movement between the first interconnecting member and the second bone abutment surface, and when in the second state, the locking feature configured to lock the first interconnecting member onto the second bone abutment surface.

41. An orthopedic implant as in claim 34, wherein the third bone abutment surface is movably joined to the second interconnecting member by a coupling that comprises a locking feature, the locking feature configured to transition from a first state to a second state, when in the first state, the locking feature configured to permit movement between the second interconnecting member and the third bone abutment surface, and when in the second state, the locking feature configured to lock the second interconnecting member onto the third bone abutment surface.

42. An orthopedic implant as in claim 34, wherein the fourth bone abutment surface is movably joined to the second interconnecting member by a coupling that comprises a locking feature, the locking feature configured to transition from a first state to a second state, when in the first state, the locking feature configured to permit movement between the second interconnecting member and the fourth bone abutment surface, and when in the second state, the locking feature configured to lock the second interconnecting member onto the fourth bone abutment surface.

43. An orthopedic implant as in claim 34, wherein a first segment of the first interconnecting member is configured to couple to the first bone abutment surface, a second segment of the first interconnecting member is configured to couple to the second bone abutment surface, a third segment of the first interconnecting member is configured to couple to the third interconnecting member, and the third segment is positioned between the first and the second segments of the first interconnecting member.

44. An orthopedic implant as in claim 34, wherein a first segment of the second interconnecting member is configured to couple to the third bone abutment surface, a second segment of the second interconnecting member is configured to couple to the fourth bone abutment surface, a third segment of the second interconnecting member is configured to couple to the third interconnecting member, and the third segment is positioned between the first and the second segments of the second interconnecting member.

45. An orthopedic implant as in claim 34, wherein the implant is at least partially comprised of a plastic material.

46. An orthopedic implant as in claim 34, wherein the implant is at least partially comprised of a metallic alloy.

47. An orthopedic implant as in claim 34, wherein the implant comprises a bioactive material configured to promote bone formation.

48. An orthopedic implant as in claim 34, wherein the implant comprises at least one bore hole configured to accept a bone fastener, the bone fastener configured to be anchored onto the first or the second bones.

49. A method for the fixation of a first vertebral bone to at least a second vertebral bone, comprising:
joining a first bone abutment surface of an orthopedic implant to a first interconnecting member thereof via a coupling, the joining comprising at least partially positioning a first surface of the coupling within a conical inner surface of a receiving seat and applying a locking force onto the coupling thereby immobilizing the first bone abutment surface relative to the first interconnecting member;
removing the locking force, the first bone abutment surface and the first interconnecting member remaining immobilized after the removal;
attaching the first bone abutment surface of the orthopedic implant to a second bone abutment surface thereof by rigidly affixing the second bone abutment surface to the first interconnecting member;

attaching a third bone abutment surface of the orthopedic implant to a fourth bone abutment surface thereof by rigidly affixing the third and fourth bone abutment surfaces to a second interconnecting member of the orthopedic implant;

aligning the bone abutment surfaces such that the first and third bone abutment surfaces face one another and the second and fourth bone abutment surfaces face one another;

movably coupling the first and the second interconnecting members using a third interconnecting member of the orthopedic implant;

positioning the first bone abutment surface of the orthopedic implant on a first side of a spinous process of the first vertebral bone, positioning the third bone abutment surface of the orthopedic implant on a second side of the spinous process of the first vertebral bone;

positioning the second bone abutment surface of the orthopedic implant on a first side of a spinous process of the second vertebral bone;

positioning the fourth bone abutment surface of the orthopedic implant on a second side of the spinous process of the second vertebral bone;

applying a force onto the orthopedic implant, the force urging the first bone abutment surface towards the third bone abutment surface and capturing the spinous process of the first vertebral bone there between; and transitioning a locking mechanism disposed at an intersection of the third interconnecting member and the first interconnecting member to a configuration limiting movement between the first and third interconnecting members.

50. A method as in claim 49, wherein the act of applying a force onto the orthopedic implant comprises utilizing a separate locking mechanism.

51. A method as in claim 49, further comprising limiting movement between the second bone abutment surface of the orthopedic implant and the first interconnecting member via a locking feature disposed at a region of attachment therebetween.

52. A method as in claim 49, further comprising limiting movement between the third bone abutment surface of the orthopedic implant and the second interconnecting member via at least a locking feature disposed at a region of attachment therebetween.

53. A method as in claim 49, further comprising limiting movement between the fourth bone abutment surface of the orthopedic implant and the second interconnecting member via at least a locking feature disposed at a region of attachment therebetween.

54. A method as in claim 49, further comprising wedging at least a portion of a second coupling within a receiving seat member, the second coupling joining the third bone abutment surface of the orthopedic implant and the second interconnecting member.

55. A method as in claim 49, further comprising wedging at least a portion of a second coupling within a receiving seat, the second coupling joining the fourth bone abutment surface of the orthopedic implant and the second interconnecting member.

56. A method as in claim 49, further comprising immobilizing three or more bones relative to one another via at least one bone fixation member.

57. A method as in claim 49, further comprising penetrating at least one bone via a tapered projection on at least one of the first and second bone abutment surfaces of the orthopedic implant.

58. A method as in claim 49, further comprising penetrating at least one bone via a tapered projection on at least one of the third and fourth bone abutment surfaces of the orthopedic implant.

59. A method as in claim 49, further comprising varying a distance of separation of the first and second bone abutment surfaces of the orthopedic along a direction of the first interconnecting member.

* * * * *